(12) United States Patent
Sugiyama et al.

(10) Patent No.: US 8,288,355 B2
(45) Date of Patent: Oct. 16, 2012

(54) SIRNA SPECIFIC TO WT1 17AA(−)ISOFORM AND USE THEREOF

(75) Inventors: Haruo Sugiyama, Suita (JP); Yusuke Oji, Suita (JP)

(73) Assignee: International Institute of Cancer Immunology, Inc., Osaka (JP)

( * ) Notice: Subject to any disclaimer, the term of this patent is extended or adjusted under 35 U.S.C. 154(b) by 723 days.

(21) Appl. No.: 12/225,745

(22) PCT Filed: Mar. 28, 2007

(86) PCT No.: PCT/JP2007/056667
§ 371 (c)(1),
(2), (4) Date: Apr. 14, 2009

(87) PCT Pub. No.: WO2007/119564
PCT Pub. Date: Oct. 25, 2007

(65) Prior Publication Data
US 2011/0190384 A1    Aug. 4, 2011

(30) Foreign Application Priority Data

Mar. 29, 2006 (JP) ................................. 2006-092214

(51) Int. Cl.
*C12N 15/11* (2006.01)
*C12N 15/00* (2006.01)
*C07H 21/02* (2006.01)
(52) U.S. Cl. .................... 514/44 A; 536/24.5; 435/320.1
(58) Field of Classification Search .................... None
See application file for complete search history.

(56) References Cited

U.S. PATENT DOCUMENTS

2003/0072767 A1*  4/2003  Gaiger et al. ............... 424/185.1
2003/0108524 A1*  6/2003  Diagana et al. ............. 424/93.2
2007/0287175 A1   12/2007  Sugiyama et al.

FOREIGN PATENT DOCUMENTS

WO         2006/005042 A2   1/2006

OTHER PUBLICATIONS

Buck et al. (Biotechniques, 1999, 27:528-536).*
EPO—Search Report mailed Mar. 27, 2009, for European Patent Appln. No. 07740105.7.
International Search Report and IPRP for PCT/JP2007/056667, mailed May 15, 2007.
Haber, D.A. et al., Alternative Splicing and Genomic Structure of the Wilms Tumor Gene WT1, Proceedings of the National Academy of Sciences, vol. 88, pp. 9618-9622, (1991).
Gessler, M. et al., "The Genomic Organization and Expression of the WT1 Gene", Genomics, vol. 12, pp. 807-813, (1992).
Hassen, A. et al., "Splice Variant-Specific Silencing of Angiotensin II Type 1a Receptor Messenger RNA by RNA interference in Vascular Smooth Muscle Cells", Biochemical and Biophysical Research Communications 2006, vol. 339, pp. 499-505.

Ghigna C. et al., "Cell Motility is Controlled by SF2/ASF Through Alternative Splicing of the Ron Protooncogene", Molecular Cell 2005, vol. 20, pp. 881-890.
Oji, Y. et al., "Overexpression of the Wilms' Tumor Gene WT1 in De Novo Lung Cancers", Int. J. Cancer 2002, vol. 100, pp. 297-303.
Siehl J. M. et al. "Expression of Wilms' Tumor Gene I at Different Stages of Acute Myeloid Leukemia and Analysis of Its Major Splice Variants", Ann. Hematol. 2004, vol. 83, pp. 745-750.
Inoue K. et al., WT1 as a New Prognostic Factor and a New Marker for the Detection of Minimal Residual Disease in Acute Leukemia, Blood 1994, vol. 84, pp. 3071-3079.
Inoue K. et al., Aberrant Overexpression of the Wilms Tumor Gene (WT1) in Human Leukemia, Blood 1997, vol. 89, pp. 1405-1412.
Yamagami T. et al., "Growth Inhibition of Human Leukemic Cells by WT1 (Wilms Tumor Gene) Antisense Oligodeoxynucleotides: Implications for the Involvement of WT1 in Leukemogenesis" Blood 1996, vol. 87, pp. 2878-2884.
Inoue K. et al., "Wilms' Tumor Gene (WT1) Competes with Differentiation-Inducing Signal in Hematopoietic Progenitor Cells", Blood 1998, vol. 91, pp. 2969-2976.
Oji Y. et al., "Expression of the Wilms' Tumor Gene WT1 in Solid Tumors and Its Involvement in Tumor Cell Growth", Japanese Journal of Cancer Research 1999, vol. 90, pp. 194-204.
Ueda T. et al., "Overexpression of the Wilms' Tumor Gene WT1 in Human Bone and Soft-Tissue Sarcomas", Cancer Science 2003, vol. 94, No. 3, pp. 271-276.
Oji Y. et al., "Overexpression of the Wilms' Tumor Gene WT1 in Head and Neck Squamous Cell Carcinoma", Cancer Science 2003, vol. 94, No. 6, pp. 523-529.
Oji Y. et al., "Overexpression of the Wilms' Tumor Gene WT1 in Primary Thyroid Cancer", Cancer Science 2003, vol. 94, No. 7, pp. 606-611.
Oji Y. et al., "Overexpression of the Wilms' Tumor Gene WT1 in Colorectal Adenocarcinoma", Cancer Science 2003, vol. 94, No. 8, pp. 712-717.
Oji Y. et al., "Absence of Mutations in the Wilms' Tumor Gene WT1 in De Novo Non-Small Cell Lung Cancers", Neoplasma 2004, vol. 51.1, pp. 17-20.
Oji Y. et al. "Absence of Mutations in the Wilms' Tumor Gene WT1 in Primary Breast Cancer", Jpn. J. Clin. Oncol. 2004, vol. 34(2), pp. 74-77.
Hubinger G. et al., "Ribozyme-Mediated Cleavage of WT1 Transcripts Suppresses Growth of Leukemia Cells", Exp. Hematol. 2001, vol. 29, pp. 1226-1235.
Li H. et al., "The lck Promoter-Driven Expression of the Wilms Tumor Gene WT1 Blocks Intrathymic Differentiation of T-Lineage Cells", Int. J. Hematol 2003, vol. 77, pp. 463-470.
Ito K. et al. "Antiapoptotic Function of 17AA(+) WT1 (Wilms' Tumor Gene) Isoforms on the Intrinsic Apoptosis Pathway", Oncogene 2006, pp. 1-13.

(Continued)

Primary Examiner — Richard Schnizer
(74) Attorney, Agent, or Firm — Nixon & Vanderhye P.C.

(57) ABSTRACT

Disclosed is a polynucleotide having at least 15 contiguous bases in the base sequence of SEQ ID NO:26 and including the base sequence of SEQ ID NO:27. Also disclosed is siRNA produced based on the polynucleotide. By means of this, a cancer cell-specific molecular-targeted therapy, which successfully controls the function of WT1, can be realized.

18 Claims, 11 Drawing Sheets

OTHER PUBLICATIONS

Englert C. et al., "Induction of p21 by the Wilms' Tumor Suppressor Gene WT1", Cancer Res. 1997, vol. 57, pp. 1429-1434.

Loeb D.M. et al., "An Isoform of the Wilms' Tumor Suppressor Gene Potentiates Granulocytic Differentiation", Leukemia 2003, vol. 17, pp. 965-971.

* cited by examiner

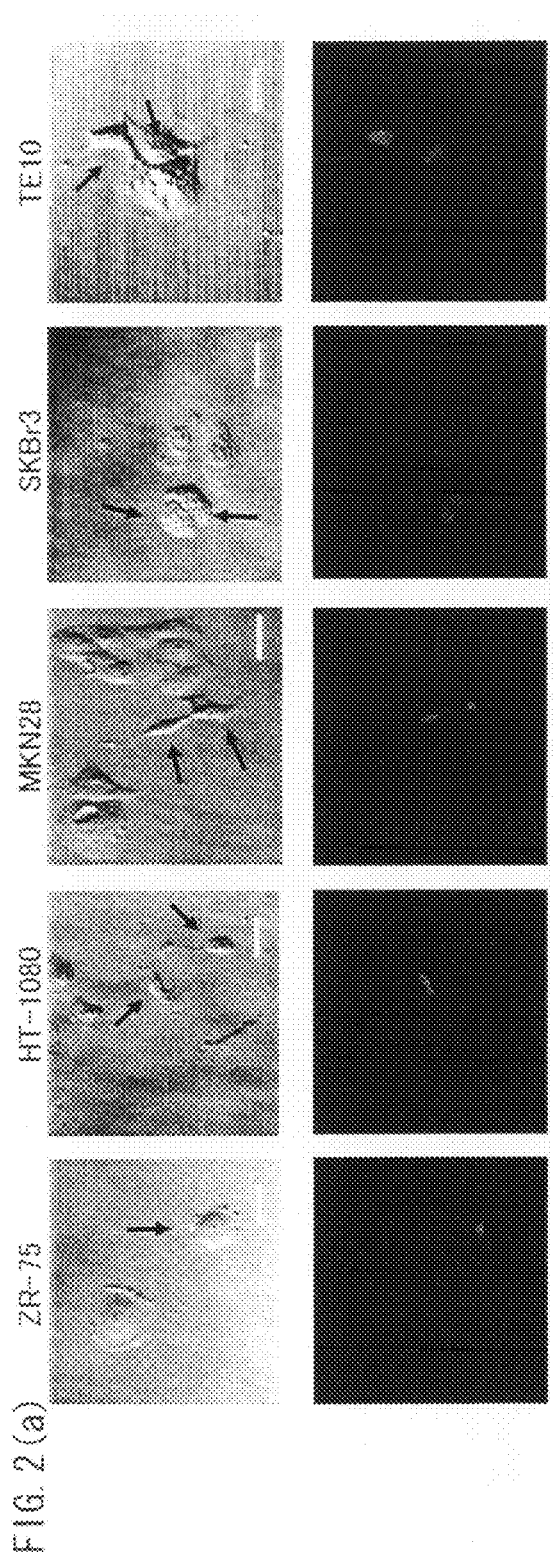
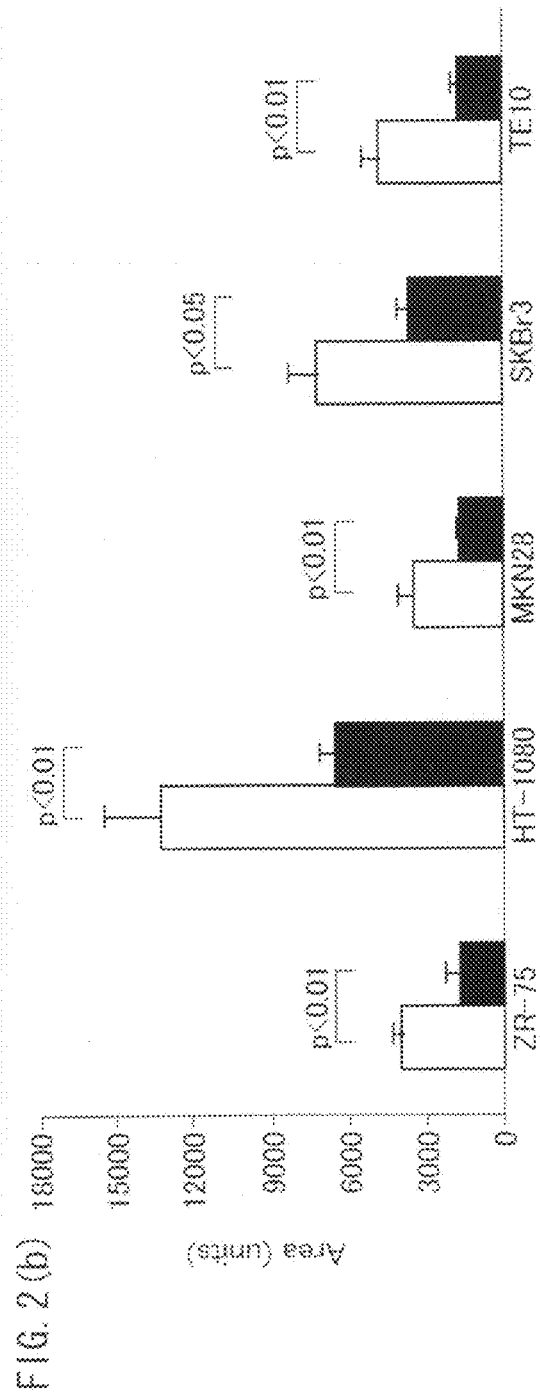
FIG. 2(a)
FIG. 2(b)

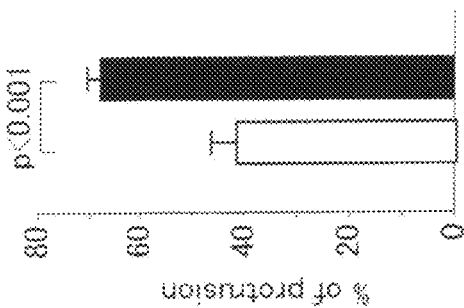
FIG. 4(a)
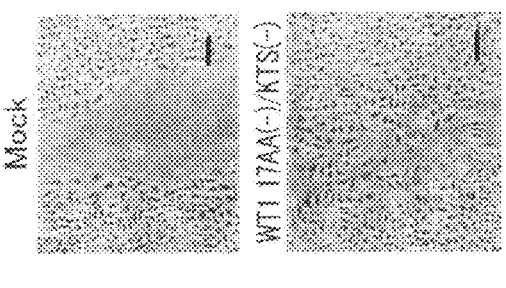
FIG. 4(b)
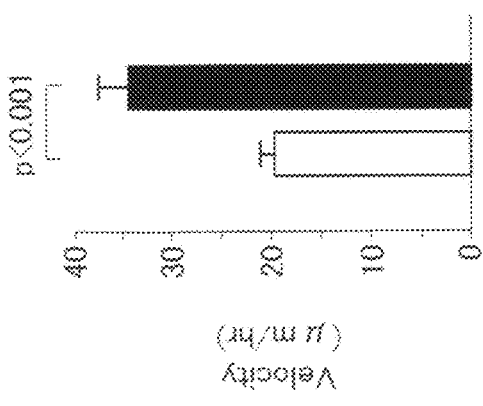
FIG. 4(c)
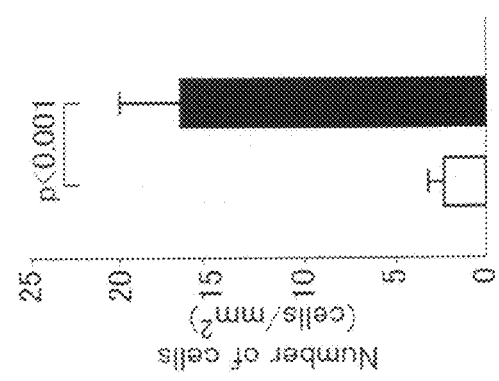
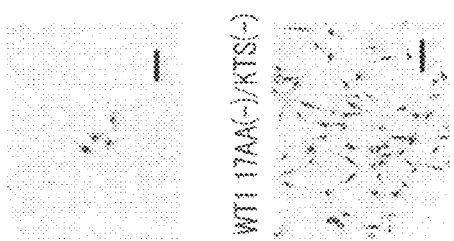

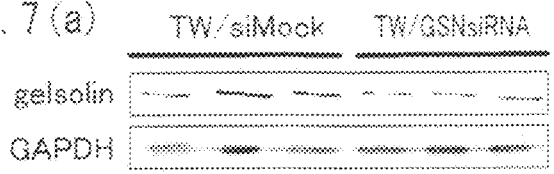
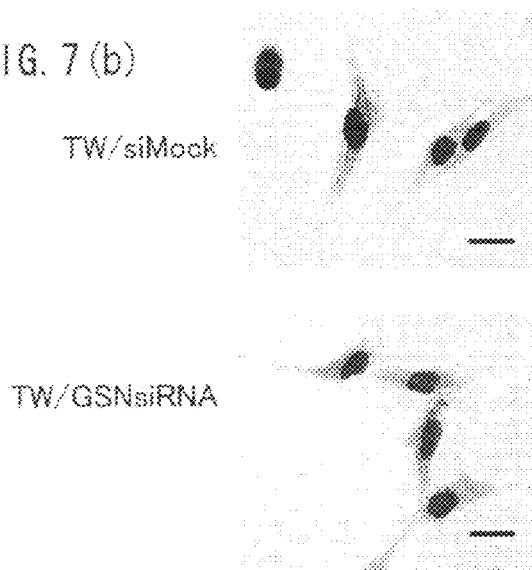
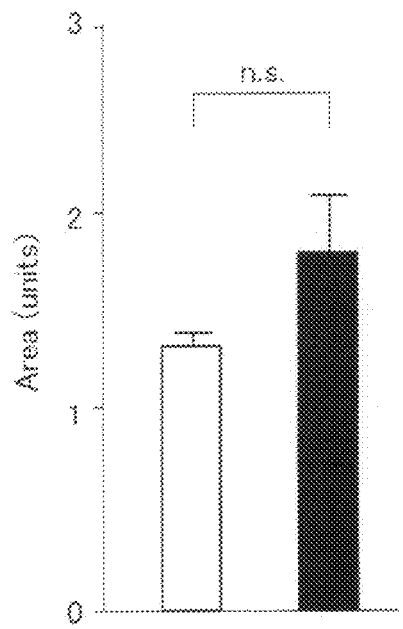
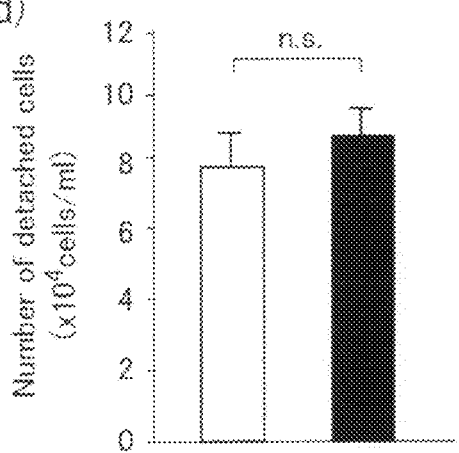
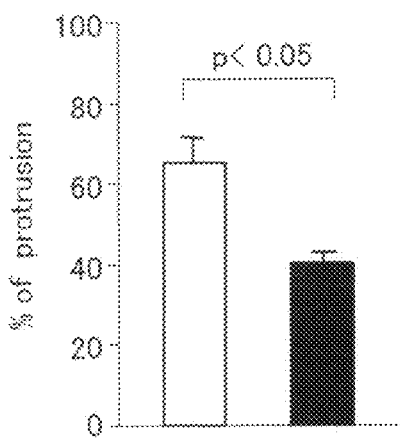
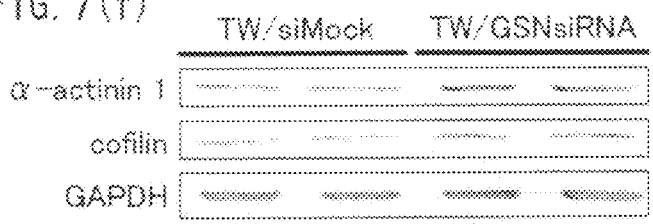

SIRNA SPECIFIC TO WT1 17AA(−)ISOFORM AND USE THEREOF

This application is the U.S. national phase of International Application No. PCT/JP2007/056667, filed 28 Mar. 2007, which designated the U.S. and claims priority to Japan Application No. 2006-092214, filed 29 Mar. 2006, the entire contents of each of which are hereby incorporated by reference.

TECHNICAL FIELD

The present invention relates to siRNA acting on a WT1 gene, and use of the siRNA. Specifically, the present invention relates to a growth suppression of solid tumor, and to an induction of cell death in the solid tumor, by means of siRNA that suppresses an expression of WT1 17AA(−) isoform.

BACKGROUND ART

Wilms' Tumor gene (WT1 gene) is a gene encoding a zinc-finger transcription factor. In the WT1 gene, it is known that an alternative splicing is occurred at 17 amino-acids site (17AA) composed of an exon 5 in the WT1 gene and at 3 amino-acids site (KTS) existing between a zinc finger 3 and a zinc finger 4 so that four isoforms (17AA(+)KTS(+), 17AA(+)KTS(−), 17AA(−)KTS(+), and 17AA(−)KTS(−)) are generated. All of the four isoforms are expressed in a human solid tumor and a leukemia cell (see Non-Patent Documents 1 and 2, for example).

The WT1 gene had been considered as a tumor suppressor gene. However, it has been found out recently that the WT1 gene functions as an oncogene. For example, the inventors of the present invention have reported that a wild-type WT1 gene that does not include a mutation in itself is highly expressed in almost all the leukemia cells, and a level of the expression has an inverse correlation with prognosis of a leukemia patient (see Non-Patent Documents 3 and 4, for example). It has been also reported by the inventors of the present invention that a growth of the leukemia cell is specifically suppressed by transducing a WT1 antisense DNA into the leukemia cell (see Non-Patent Document 5, for example), and differentiation of a mouse-originated normal myeloid precursor cell and a myeloid precursor cell line 32D c13 into a neutrophil are suppressed by a forced expression of the WT1 gene so as to grow proliferously (see Non-Patent Document 6, for example). Based on these, the inventors of the present invention have indicated that the WT1 gene is responsible for a hematopoietic lineage cell to be leukemic. Moreover, the inventors of the present invention have reported that the wild-type WT1 gene is highly expressed in various solid tumors (see Non-Patent Documents 7 through 14, for example).

The aforementioned four isoforms are considered as having different functions, respectively. For example, WT1 17AA(+)KTS(+) isoform is considered as contributing to a growth of cancer cell (see Non-Patent Document 15). WT1 17AA(+)KTS(−) isoform is considered to be responsible for a formation of a tumor of malignant lymphoma (see Non-Patent Document 16).

In recent years, the inventors of the present invention have shown that siRNA specific to WT1 17AA(+) isoform induces apoptosis of a leukemia cell expressing the WT1 gene (see Non-Patent Document 17).

[Non-Patent Document 1]
Oji Y. et al., Int. J. Cancer 100: 297 (2002)
[Non-Patent Document 2]
Siehl J. M. et al., Ann. Hematol. 83: 745 (2000)
[Non-Patent Document 3]
Inoue K. et al., Blood 84: 3071 (1994)
[Non-Patent Document 4]
Inoue K. et al., Blood 89: 1405 (1997)
[Non-Patent Document 5]
Yamaguchi T. et al., Blood 87: 2828 (1996)
[Non-Patent Document 6]
Inoue K. et al., Blood 91: 2969 (1998)
[Non-Patent Document 7]
Oji Y. et al., Japanese Journal of Cancer Research 90: 194 (1999)
[Non-Patent Document 8]
Oji Y. et al., Int J Cancer; 100: 297-303 (2002)
[Non-Patent Document 9]
Ueda T. et al., Cancer Science 94: 271 (2003)
[Non-Patent Document 10]
Oji Y. et al., Cancer Science 94: 523 (2003)
[Non-Patent Document 11]
Oji Y. et al., Cancer Science 94: 606 (2003)
[Non-Patent Document 12]
Oji Y. et al., Cancer Science 94: 712 (2003)
[Non-Patent Document 13]
Oji Y. et al., Neoplasma 51: 17 (2004)
[Non-Patent Document 14]
Oji Y. et al., Jpn. J. Clin. Oncol. 34: 74 (2004)
[Non-Patent Document 15]
Hubinger G. et al., Exp Hematol 10: 1226-1235 (2001)
[Non-Patent Document 16]
Li H. et al., Int J Hematol 77: 463-470 (2003)
[Non-Patent Document 17]
Ito K. et al., Oncogene; March 6: 1 (2006)
[Non-Patent Document 18]
Englert C. et al., Cancer Res 8: 1429-1434 (1997)
[Non-Patent Document 19]
Loeb D. M. et al., Leukemia 17: 965-971 (2003)

DISCLOSURE OF INVENTION

As described above, it is considered to be possible to apply a molecular-targeted therapy specifically to a cancer cell by suppressing a function of WT1 that has a function like an oncogene. However, a technique using antisense oligo-DNA or a ribozyme, which is used as a conventional method for suppressing an expression of the WT1 gene, could not have attained a high efficiency in suppressing the expression of the WT1 gene, or a high specificity, to a sufficient extent.

The present invention is accomplished in view of the problems above, and an object of the present invention is to achieve a cancer cell-specific molecular-targeted therapy that successfully controls the function of the WT1.

As mentioned above, it has been indicated that WT1 17AA (+) isoform has a function like an oncogene. However, a function of WT1 17AA(−)KTS(+) isoform has not been determined. Meanwhile, it has been reported that the 17AA (−)KTS(−) isoform induces G1 arrest in an osteosarcoma cell (see Non-Patent Document 18), and promotes a differentiation by inhibiting G1/S transition in a cell of myeloid precursor cell line 32D c13 (see Non-Patent Document 19). Moreover, siRNA specific to WT1 17AA(−) isoform does not induce apoptosis of a WT1-expressing leukemia cell line or a WT1-nonexpressing lymphoma cell line (see Non-Patent Document 17).

The inventors of the present invention have demonstrated in first that, in a cell from a solid tumor, WT1 17AA(−)KTS (−) isoform fulfills an oncogene-like function to change a cytoskeleton by controlling an expression level of an actin-binding protein (cofilin, actinin, and gelsolin) so as to induce a change in shape of the cell, an enhancement in cell movement in vitro, and an enhancement in ability of cell invasion. Further, the inventors of the present invention have found that a cell death can be induced specifically in a tumor cell by specifically inhibiting an expression of the WT1 17AA(−) isoform. Based on these, the present invention is accomplished.

That is, the polynucleotide according to the present invention is a polynucleotide having at least 15 contiguous bases in the base sequence of SEQ ID NO:26 and including the base sequence of SEQ ID NO:27. It is preferable to arrange so that the polynucleotide has the base sequence of SEQ ID NO:26.

With the arrangement, the polynucleotide according to the present invention can provide siRNA that can specifically inhibit an expression of WT1 17AA(−) isoform without inhibiting an expression of WT1 17AA(+) isoform.

The medical composition according to the present invention is a medical composition for treating a solid tumor, comprising any one of: double-stranded RNA composed of (i) first RNA encoded by DNA complementary to a polynucleotide having at least 15 contiguous bases in the base sequence of SEQ ID NO:26 and including the base sequence of SEQ ID NO:27 and (ii) second RNA capable of paring with the first RNA; DNA encoding the double-stranded RNA; and a vector to which the DNA is inserted.

Considering past reports on the WT1 17AA(−) isoform, it could not have been expected that siRNA which specifically inhibits an expression of the WT1 17AA(−) isoform, which has been regarded as functioning as a tumor suppressor gene, fulfills a tumor-suppressing function.

It is preferable to arrange the medical composition according to the present invention so that DNA encoding the second RNA hybridizes under a stringent condition with the polynucleotide having at least 15 contiguous bases in the base sequence of SEQ ID NO:26 and including the base sequence of SEQ ID NO:27.

It is preferable to arrange the medical composition according to the present invention so that the second RNA includes at least 15 contiguous bases in the base sequence of SEQ ID NO:29.

It is preferable to arrange the medical composition according to the present invention so that the first RNA includes at least 15 contiguous bases in the base sequence of SEQ ID NO:30.

It is preferable to arrange the medical composition according to the present invention so that the DNA encoding the double-stranded RNA includes the base sequence of SEQ ID NO:27.

It is preferable to arrange the medical composition according to the present invention so that the double-stranded RNA is composed of a paring of RNA including the base sequence of SEQ ID NO:29 with RNA including the base sequence of SEQ ID NO:30.

It is preferable that the cell to which the medical composition according to the present invention can be applied is selected from a group including bladder cancer, kidney cancer, cutaneous squamous cell cancer, head and neck cancer (cutaneous squamous cell cancer of the head and neck, for example), lung cancer (non-small-cell lung cancer (NSCLC), for example), alimentary canal tumor (esophagus tumor, stomach cancer, small intestinal tumor, large intestinal tumor), glioma, mesothelial tumor, and the like.

The medical kit according to the present invention is a medical kit for treating a solid tumor, comprising any one of: double-stranded RNA composed of (i) first RNA encoded by DNA complementary to a polynucleotide having at least 15 contiguous bases in the base sequence of SEQ ID NO:26 and including the base sequence of SEQ ID NO:27 and (ii) second RNA capable of paring with the first RNA; DNA encoding the double-stranded RNA; and a vector to which the DNA is inserted.

The method according to the present invention is a method for treating a solid tumor, comprising the step for administering, to a cell forming the solid tumor, double-stranded RNA composed of (i) first RNA encoded by DNA complementary to a polynucleotide having at least 15 contiguous bases in the base sequence of SEQ ID NO:26 and including the base sequence of SEQ ID NO:27 and (ii) second RNA capable of paring with the first RNA, in such a way that the double-stranded RNA will be expressed in the cell.

It is preferable to arrange the method according to the present invention so that the step for administering is carried out by transducing, into the target cell, a vector to which a polynucleotide including DNA encoding the first RNA and DNA encoding the second RNA is inserted.

The cell death-inducing agent according to the present invention is a cell death-inducing agent for treating a solid tumor, comprising any one of: double-stranded RNA composed of (i) first RNA encoded by DNA complementary to a polynucleotide having at least 15 contiguous bases in the base sequence of SEQ ID NO:26 and including the base sequence of SEQ ID NO:27 and (ii) second RNA capable of paring with the first RNA; DNA encoding the double-stranded RNA; and a vector to which the DNA is inserted.

It is preferable to arrange the cell death-inducing agent according to the present invention so that DNA encoding the second RNA hybridizes under a stringent condition with the polynucleotide having at least 15 contiguous bases in the base sequence of SEQ ID NO:26 and including the base sequence of SEQ ID NO:27.

It is preferable to arrange the cell death-inducing agent according to the present invention so that the second RNA includes at least 15 contiguous bases in the base sequence of SEQ ID NO:29.

It is preferable to arrange the cell death-inducing agent according to the present invention so that the first RNA includes at least 15 contiguous bases in the base sequence of SEQ ID NO:30.

It is preferable to arrange the cell death-inducing agent according to the present invention so that the DNA encoding the double-stranded RNA includes the base sequence of SEQ ID NO:27.

It is preferable to arrange the cell death-inducing agent according to the present invention so that the double-stranded RNA is composed of a paring of RNA including the base sequence of SEQ ID NO:29 with RNA including the base sequence of SEQ ID NO:30.

It is preferable that the cell to which the cell death-inducing agent according to the present invention can be applied is selected from a group including bladder cancer, kidney cancer, cutaneous squamous cell cancer, head and neck cancer (cutaneous squamous cell cancer of the head and neck, for example), lung cancer (non-small-cell lung cancer (NSCLC), for example), alimentary canal tumor (esophagus tumor, stomach cancer, small intestinal tumor, large intestinal tumor), glioma, mesothelial tumor, and the like.

The cell death-inducing kit according to the present invention is a cell death-inducing kit for inducing apoptosis of a cell forming a solid tumor, comprising any one of: double-stranded RNA composed of (i) first RNA encoded by DNA complementary to a polynucleotide having at least 15 contiguous bases in the base sequence of SEQ ID NO:26 and including the base sequence of SEQ ID NO:27 and (ii) second RNA capable of paring with the first RNA; DNA encoding the double-stranded RNA; and a vector to which the DNA is inserted.

The method for inducing a cell death according to the present invention is a method for inducing apoptosis of a cell forming a solid tumor, comprising the step for administering, to the cell, double-stranded RNA composed of (i) first RNA encoded by DNA complementary to a polynucleotide having at least 15 contiguous bases in the base sequence of SEQ ID NO:26 and including the base sequence of SEQ ID NO:27 and (ii) second RNA capable of paring with the first RNA, in such a way that the double-stranded RNA will be expressed in the cell.

It is preferable to arrange the method for inducing a cell death according to the present invention so that the step for administering is carried out by transducing, into the target cell, a vector to which a polynucleotide including DNA encoding the first RNA and DNA encoding the second RNA is inserted.

For a fuller understanding of other objects, characteristics, and advantages of the present invention, reference should be made to the ensuing detailed description. The advantages of the present invention could be specified with the description taken in conjunction with the accompanying drawings.

BRIEF DESCRIPTION OF DRAWINGS

FIG. 1(a) shows, as an example, results of Western blotting showing the presence or absence of expressions of WT1 proteins in four TYK cell lines (each being transduced with one of four different WT1 isoforms).

FIG. 1(b) shows, as an example, a change in cell morphology caused by stable expressions of each WT1 isoform in TYK cells.

FIG. 1(c) shows averages of relative areas of eight or more individual cells obtained from three cell clones.

FIG. 2(a) is a view showing a morphological change of various types of cancer cells induced by a constitutive expression of WT1 17AA(−)/KTS(−) isoform. In FIG. 2(a), various types of cancer cells (ZR-75, HT-1080, MKN28, SKBr3, and TE10, for example) in which GFP-tagged WT1 17AA(−)/KTS(−) isoform was transiently expressed were morphologically analyzed by using a confocal microscope 48 to 72 hours after transfection.

FIG. 2(b) is a view showing a morphological change of various types of cancer cells induced by a constitutive expression of WT1 17AA(−)/KTS(−) isoform. FIG. 2(b) shows averages of relative areas of nine or more individual cells.

FIG. 4(a) is a view showing an enhancement of cell migration induced by a constitutive expression of WT1 17AA(−)/KTS(−) isoform. Movements of individual TYK cells expressing GFP-WT1 17AA(−)/KTS(−) isoform and individual TYK cells not expressing GFP-WT1 17AA(−)KTS(−) isoform were recorded for 5 hours at intervals of 2 minutes by using a Time-lapse video recorder. Velocity of the movements of the cells was calculated.

FIG. 4(b) is a view showing an enhancement of cell migration induced by a constitutive expression of WT1 17AA(−)/KTS(−) isoform. TYK cells (■) transduced with a WT1 17AA(−)/KTS(−) isoform expression vector and TYK cells (□) transduced with a control vector were analyzed in regard to collective migration by using a wound-healing assay.

FIG. 4(c) is a view showing an enhancement of cell migration induced by a constitutive expression of WT1 17AA(−)/KTS(−) isoform. TYK cells (■) transduced with a WT1 17AA(−)/KTS(−) isoform expression vector and TYK cells (□) transduced with a control vector were analyzed in regard to chemotaxis toward Delbucco's modified Eagle's medium including 5% FBS by using a Transwell Migration assay.

FIG. 5(a) shows a result of immunohistochemical staining for F-actin, vinculin (focal adhesion protein), and nuclei in a TYK cell transduced with the WT1 17AA(−)/KTS(−) isoform and in a TYK cell transduced with a control vector.

FIG. 6(a) shows expression levels of α-actinin and cofilin, which were determined by Western blotting.

FIG. 6(b) shows the cells stained with May Grunwald-Giemsa.

FIG. 6(c) shows cell areas calculated by NIH Image software (1: TW/Mock cell clone; 2 and 3: different TW/ACTN-CFL cell clones, respectively).

FIG. 6(d) shows a cell-substratum adhesion determined by a detachment assay.

FIG. 6(e) shows a collective cell migration analyzed by a wound-healing assay. The cell migration is represented as an average of the ratio (percentage) of length of protrusion to width of first detachment of cells at three different sites.

FIG. 6(f) shows an expression level of gelsolin, which was determined by Western blotting.

FIG. 7(a) is a view showing that a suppression of gelsolin expression reduced a cell migration, however, did not affect cell morphology or a cell-substratum adhesion. A gelsolin-specific siRNA vector (TW/GSNsiRNA) or a control vector (TW/siMock) was transduced into TYK cells transduced with WT1 17AA(−)/KTS(−) isoform. FIG. 7(a) shows an expression level of gelsolin protein, which was determined by Western blotting.

FIG. 7(b) is a view showing that a suppression of gelsolin expression reduced a cell migration, however, did not affect cell morphology or a cell-substratum adhesion. A gelsolin-specific siRNA vector (TW/GSNsiRNA) or a control vector (TW/siMock) was transduced into TYK cells transduced with WT1 17AA(−)/KTS(−) isoform. FIG. 7(b) shows the cells stained with May Grunwald-Giemsa.

FIG. 7(c) is a view showing that a suppression of gelsolin expression reduced a cell migration, however, did not affect cell morphology or a cell-substratum adhesion. A gelsolin-specific siRNA vector (TW/GSNsiRNA) or a control vector (TW/siMock) was transduced into TYK cells transduced with WT1 17AA(−)/KTS(−) isoform. FIG. 7(c) shows the areas of the TW/Mock cell clone and the TW/GSNsiRNA cell clone, which were calculated by NIH Image software.

FIG. 7(d) is a view showing that a suppression of gelsolin expression reduced a cell migration, however, did not affect cell morphology or a cell-substratum adhesion. A gelsolin-specific siRNA vector (TW/GSNsiRNA) or a control vector (TW/siMock) was transduced into TYK cells transduced with WT1 17AA(−)/KTS(−) isoform. FIG. 7(d) shows a cell-substratum adhesion determined by a detachment assay.

FIG. 7(e) is a view showing that a suppression of gelsolin expression reduced a cell migration, however, did not affect cell morphology or a cell-substratum adhesion. A gelsolin-specific siRNA vector (TW/GSNsiRNA) or a control vector (TW/siMock) was transduced into TYK cells transduced with WT1 17AA(−)/KTS(−) isoform. FIG. 7(e) shows a collective cell movement analyzed by a wound-healing assay.

FIG. 7(f) is a view showing that a suppression of gelsolin expression reduced a cell migration, however, did not affect cell morphology or a cell-substratum adhesion. A gelsolin-specific siRNA vector (TW/GSNsiRNA) or a control vector (TW/siMock) was transduced into TYK cells transduced with WT1 17AA(−)/KTS(−) isoform. FIG. 7(f) shows expression levels of α-actinin 1 and cofilin, which were determined by Western blotting.

BEST MODE FOR CARRYING OUT THE INVENTION

[1] WT1 17AA(−) Isoform-Specific siRNA

Figure 1A:
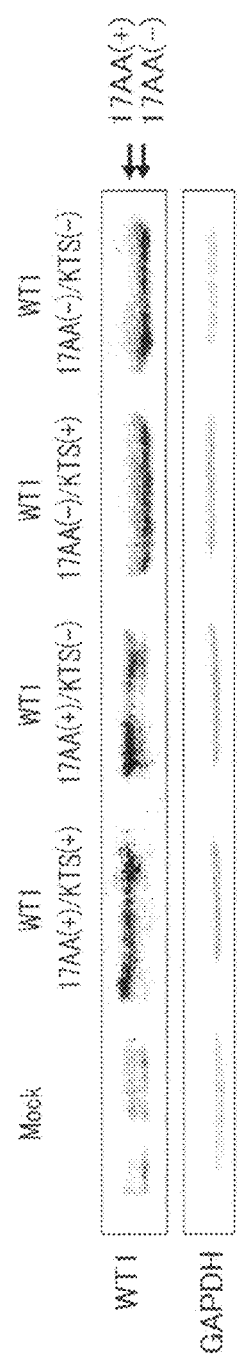
FIG. 1(a) is a view showing a morphological change of TYK ovary cancer cell induced by a constitutive expression of WT1 17AA(−)/KTS(−) isoform.

The present invention relates to a polynucleotide for providing WT1 17AA(−) isoform-specific siRNA.

Recently, an RNA interference (RNAi) technique draws much attention as a molecular-targeted therapy. The RNAi, which is initiated with double-stranded DNA (dsDNA), is a post-transcriptional gene silencing process in which siRNA causes a degradation of its homologous RNA, which is carried out sequence-specifically.

The siRNA is required to be long enough to carry out a gene-specific suppression of expression. At the same time, the siRNA is required to be short enough to avoid adverse influences on a mammalian cell. Thus, the siRNA is preferably a nucleotide base pair having 15 to 49 base length, more preferably a nucleotide base pair having 15 to 30 base length.

Therefore, the polynucleotide in accordance with the present invention has at least 15 contiguous bases in the base sequence of SEQ ID NO:26 and includes the base sequence of SEQ ID NO:27. As mentioned above, it is known that an alternative splicing is occurred at two sites in a WT1 gene so that four isoforms, which are 17AA(+)KTS(+) (SEQ ID NO:32 and 33), 17AA(+)KTS(−) (SEQ ID NO:34 and 35), 17AA(−)KTS(+) (SEQ ID NO:36 and 37), and 17AA(−)KTS(−) (SEQ ID NO:38 and 39), are generated. Since the base sequences of SEQ ID NO:26 and SEQ ID NO:27 are generated by an alternative splicing at the 17AA site, the polynucleotide in accordance with the present invention can provide, with the arrangement above, siRNA capable of specifically inhibiting an expression of WT1 17AA(−) isoform without inhibiting an expression of WT1 17AA(+) isoform.

When used in the present specification, the term "polynucleotide" means a polymer of nucleotides, and is used interchangeably with "gene", "nucleic acid", or "nucleic acid molecule". Also, the term "base sequence" used in the present specification means a sequence of deoxyribonucleotides (abbreviated to A, G, C, and T), and is used interchangeably with "nucleic acid sequence" or "nucleotide sequence".

The polynucleotide in accordance with the present invention may exist in the form of RNA (mRNA, for example) or DNA (cDNA or genomic DNA, for example). The DNA may be double-stranded or single-stranded. The single-stranded DNA or single-stranded RNA may be a coding strand (known as a sense strand) or a noncoding strand (known as an antisense strand).

A short polynucleotide is represented as a dinucleotide (dimmer) and a trinucleotide (trimer). A long polynucleotide is represented by using the number of polymerized nucleotides, in such a manner as 30mer or 100mer. The polynucleotide in accordance with the present invention may be produced as a fragment of a longer polynucleotide or may be chemically synthesized.

It is preferable that the siRNA produced with the polynucleotide in accordance with the present invention is double-stranded RNA composed of (i) first RNA encoded by DNA complementary to a polynucleotide having at least 15 contiguous bases in the base sequence of SEQ ID NO:26 and including the base sequence of SEQ ID NO:27 and (ii) second RNA capable of paring with the first RNA. However, the siRNA may be supplied as DNA encoding the double-stranded RNA or as a vector to which the DNA encoding the double-stranded RNA is inserted.

When used in the present specification, the term "WT1 17AA(−) isoform-specific siRNA" is used interchangeably with "17AA(−) siRNA". With the polynucleotide being provided as a target sequence, 17AA(−) siRNA can be easily produced by any methods known in the art. The 17AA(−) siRNA may be chemically synthesized or produced by a recombinant expression, for example.

As described above, the 17AA(−) siRNA is preferably a nucleotide base pair having 15 to 49 base length, more preferably a nucleotide base pair having 15 to 30 base length. It should be noted that, in the present specification, strands of the siRNA do not have to be completely paired with each other, except at a region where the strands pair with each other as dsRNA, and the siRNA may include unpaired sites occurred due to a mismatched base pair and the like.

In addition, the 17AA(−) siRNA may or may not have a protrusion at its ends. In case of the 17AA(−) siRNA having the protrusion, the number of bases included in the protrusion is not limited as long as an RNAi effect can be induced.

In the 17AA(−) siRNA, it is preferable that DNA encoding the second RNA can hybridize under a stringent condition with the polynucleotide having at least 15 contiguous bases in the base sequence of SEQ ID NO:26 and including the base sequence of SEQ ID NO:27.

The hybridization can be carried out by a well-known method such as one described in Sambrook et al., Molecular Cloning, A Laboratory Manual, $2^{nd}$ Ed., Cold Spring Harbor Laboratory (1989). In general, with the higher temperature or the higher salt concentration, the higher stringency (a more difficult condition for hybridization), which enables to obtain polynucleotides having a higher homology, can be provided. A suitable temperature for hybridization differs depending on a factor such as a base sequence and a length of the base sequence. For example, in case where a DNA fragment composed of 18 bases encoding 6 amino acids is used as a probe, it is preferable to arrange the temperature to be 50° C. or below.

When used in the present specification, the wording "a stringent condition for hybridization" means such a condition that polynucleotides are incubated overnight at 42° C. in a hybridization solution (50% formamide, 5×SSC (including 150 mM NaCl, 15 mM trisodium citrate), 50 mM sodium phosphate (pH7.6), 5×Denhardt's solution, 10% dextran sulfate, and 20 µg/ml denatured fragmented salmon sperm DNA), and then a filter is washed in 0.1×SSC at approximately 65° C. A polynucleotide that "partly" hybridizes to other polynucleotide intends a polynucleotide (either DNA or RNA) that hybridizes to at least 15 nucleotides (nt), preferably at least approximately 20 nt, more preferably at least approximately 30 nt, further preferably more than 30 nt of a reference polynucleotide. The polynucleotide that "partly" hybridizes to other polynucleotide is also useful for a probe for detection.

In case where the 17AA(−) siRNA is supplied as dsRNA, it is preferable that the 17AA(−) siRNA is composed of paring of RNA including the base sequence of SEQ ID NO:29 with RNA including the base sequence of SEQ ID NO:30.

In case where the 17AA(−) siRNA is supplied as DNA encoding the siRNA or as a vector to which the DNA is inserted, it is preferable that the second RNA includes at least 15 contiguous bases in the base sequence of SEQ ID NO:29, and the first RNA includes at least 15 contiguous bases in the base sequence of SEQ ID NO:30. Further, it is preferable that the first RNA and the second RNA (or DNA encoding the first RNA or the second RNA) are combined with each other via a polynucleotide composed of the base sequence of SEQ ID NO:31 so as to form the hairpin (stem-loop) RNA. However, the present embodiment is not limited to this.

By using a siRNA expression vector, that is, a DNA vector obtained by inserting, as a foreign DNA fragment, DNA that corresponds to the siRNA, it is possible to make the 17AA(−) siRNA express and act in the body effectively. Such a DNA vector may be selected accordingly from various vector series that are known in the art. Note that the DNA fragment that corresponds to the 17AA(−) siRNA can be easily prepared by a method known in the art.

As the expression vector above, known is such a "hairpin type" or "stem-loop type" vector that a DNA sequence corresponding to a sense strand of the siRNA and a DNA sequence corresponding to an antisense strand of the siRNA are encoded in one DNA strand at downstream of a promoter. The DNA fragment that is inserted to such a vector produces hairpin type (stem-loop type) RNA after being transcribed in the body, and produces the siRNA as a result of enzyme reactions.

The siRNA expression vector can be easily produced by using a method known by persons skilled in the art. Such an expression vector may be, but not limited to, various types of virus vectors (adenovirus vector, adeno-associated virus vector, and the like), for example. The adenovirus vector enables to transduce a gene into a cell having a slow rate of cell division (a nerve cell and the like, for example), and achieves a high-efficiency transducing.

RNA is in itself an unstable substance, and is degraded by a ribonuclease and the like when being injected to the blood. However, the 17AA(−) siRNA can be applied to a treatment of solid tumor by using Drug Delivery System (DDS), which is known in the art, and the like. The 17AA(−) siRNA is encapsulated in a carrier such as a functional liposome, a polymer micelle, and the like, or is modified with PEG and the like at its both ends so as to be stable in the blood and/or cell.

[2] Use of WT1 17AA(−) Isoform-Specific siRNA (1) Medical Composition

The present invention provides a medical composition that comprises WT1 17AA(−) isoform-specific siRNA (17AA(−) siRNA). The medical composition in accordance with the present invention is efficient in a treatment of solid tumor.

It is preferable that the medical composition in accordance with the present invention comprises either one of: double-stranded RNA having first RNA encoded by DNA complementary to polynucleotide being composed of at least 15 contiguous bases in the base sequence of SEQ ID NO:26 and including the base sequence of SEQ ID NO:27, and second RNA capable of paring with the first RNA; DNA encoding the double-stranded RNA; and a vector to which the DNA is inserted.

"Tumor" is known as a neoplasm, and is a new growth including a neoplasm cell. In addition, the "neoplasm cell" is also known as a cell having a growth problem, and intends a cell that grows proliferously at extremely high speed. The neoplasm is an abnormally-growing tissue, and in general, separately forms an aggregation. The aggregations grow more rapidly than a normally-growing tissue. The neoplasm partly or entirely has defects in forming a structure in combination with a normal tissue, and/or in functioning in cooperation with the normal tissue.

The tumor may be benign (benign tumor) or malignant (malignant tumor or cancer). The malignant tumor can be categorized into three main types. A malignant tumor developing in an epithelial structure is described as carcinoma. A malignant tumor originated in connective tissues such as muscles, cartilage tissues, fats, or bones is described as sarcoma. A malignant tumor affecting a hematopoietic structure (structure responsible for production of blood cells) including immune system components is described as leukemia or lymphoma. Other neoplasm may be, but not limited to, neurofibroma.

The cancer (tumor) can be divided into the following two types: 1) one growing at the same time as moving constantly in the blood after becoming malignant, and spreading to hematopoietic tissues and other organs all over the body, although being a hemtopoietic tissue or a lymphatic tissue (e.g., leukemia); 2) one existing in a particular tissue or organ as a tumor mass (e.g., many tumors other than leukemia). When used in the present specification, the term "solid tumor" means a tumor other than leukemia. The solid tumor to which the medical composition in accordance with the present invention can be applied intends particularly a bladder cancer, a kidney cancer, a cutaneous squamous cell cancer, a head and neck cancer (cutaneous squamous cell cancer of the head and neck, for example), a lung cancer (non-small-cell lung cancer (NSCLC), for example), an alimentary canal tumor (esophagus tumor, stomach cancer, small intestinal tumor, large intestinal tumor), glioma, a mesothelial tumor, and the like.

When used in the present specification, the term "treatment" means a relief or elimination of a symptom, and includes any process carried out prophylactically (before the onset of the symptom) and therapeutically (after the onset of the symptom). The wording "treat a solid tumor" means suppressing or preventing a growth (proliferation) of the solid tumor. The wording "treat a solid tumor" also intends that, by using a method for processing the solid tumor, the solid tumor becomes lighter in weight and smaller in size than the same tumor to which the method is not applied. It is preferable that the growth (proliferation) of the solid tumor is suppressed to such an extent that the tumor exhibits net decrease in weight and size.

The composition comprising the siRNA or the siRNA expression vector as an active constituent may comprise an arbitrary constituent, such as a buffer and/or adjuvant, which is known by persons skilled in the art, according to an object or constituents of the composition.

The medical composition in accordance with the present invention preferably has such a form that the composition can exist at a high concentration in the blood. That is to say, the medical composition preferably has an "injectable form", which is appropriate for an injection into a vein, a muscle, an abdominal cavity, a breastbone, and a joint, and for a subcutaneous injection. However, this is not only possibility. For example, the medical composition may be an oral agent such as a tablet, a capsule (including a soft capsule and a microcapsule, and preferably being an extended-release capsule), a powdered medicine, granules, and syrup, or may be a parenteral agent such as an injection, a suppository, a pellet, and drops. The medical composition in accordance with the present invention can be administered orally and parenterally because of its low toxicity. When used in the present specification, the term "parenteral" represents a type of administration, which includes an injection and infusion into a vein, a muscle, an abdominal cavity, a breastbone, and a joint, and a subcutaneous injection and infusion.

The medical composition in accordance with the present invention can be administered in an appropriate route according to its pharmaceutical form. A method for administration is not particularly limited, and can be carried out internally and externally, and also carried out by injection. The injection solution can be administered into a vein and a muscle, and administered intradermally and subcutaneously.

The medical composition in accordance with present invention can be produced by a method known in the pharmaceutical field. An amount of the 17AA siRNA in the medical composition in accordance with the present invention is not particularly limited, provided that the 17AA siRNA is administered, by taking into consideration the form and the method of administration, within the after-mentioned range by using the medical composition in accordance with the present invention.

Note that, in general, a composition may be either one of a composition comprising a substance A singularly, a single composition comprising the substance A and a substance B, and a combination of a composition comprising the substance A singularly and a composition comprising the substance B singularly. These compositions may comprise constituents (such as a carrier that can be accepted as a pharmaceutical agent) other than the substances A and B. When the composition comprising the 17AA(−) siRNA is used in combination with a composition comprising other constituent (the substance B), these compositions cannot be regarded as one composition as a whole, since the medical composition in accordance with the present invention is characterized by comprising the 17AA(−) siRNA, which is described as the substance A. However, such a combination of compositions can be regarded as "kit" to be hereinafter described. It is easily understood by persons skilled in the art that the combination can be provided as a kit, not as a composition.

Note that persons skilled in the art, who read the present specification, easily understand that a method for treating the solid tumor, which includes a step for administering the 17AA(−) siRNA to a subject, is also within the scope of the present invention.

(2) Medical Kit

The present invention also provides a medical kit including the 17AA(−) siRNA. When used in the present specification, the term "kit" means a package including a container (such as a bottle, a plate, a tube, and a dish) for containing a certain material therein. It is preferable that the kit has an instruction for use of the material. When used for referring the kit in the present specification, the term "including" means containing in either one of individual containers constituting the kit. The medical kit in accordance with present invention may be a package for packing a number of different compositions together. The composition have any of the forms described above, and may be contained in the container when in the form of solution. The medical kit in accordance with the present invention may include the substances A and B in one container or in separate containers. The "instruction" may have any form as being printed or written on a paper or any other media, or recorded an electronic media such as a magnetic tape, a computer read-around disk or tape, and CD-ROM. In addition, the medical kit in accordance with the present invention may include a container that contains a diluent, a solvent, a washing fluid, or other reagents. Moreover, the medical kit in accordance with the present invention may include any instrument required for applying the kit to a method for medical treatment.

Persons skilled in the art, who read the present specification, easily understands that the 17AA(−) siRNA and other substances in the medical kit in accordance with the present invention can be used according to a usage form of the composition.

(3) Method for Medical Treatment

The present invention further provides a method for medical treatment. The method in accordance with the present invention includes a step for administering the compound in accordance with present invention to a subject.

Persons skilled in the art, who read the present specification, easily understand that the 17AA(−) siRNA and other substances in the method in accordance with the present invention can be used according to a usage form of the composition.

Since the WT1 gene is highly expressed in a cancer cell, a cell death induced by suppression of 17AA(−) isoform expression occurs specifically in the cancer cell, and not in a normal cell. Therefore, it is possible to carry out a cancer cell-specific molecular-targeted therapy by using the present invention.

In the present specification, the treatment of the solid tumor is taken as an example of use of the WT1 17AA(−) isoform-specific siRNA. In the light of the fact that the WT1 17AA(−) isoform-specific siRNA induces apoptosis in a cell forming the solid tumor, persons skilled in the art, who read the present specification, easily understand that the present invention encompasses a cell death-inducing agent for inducing apoptosis in the cell forming the solid tumor, a kit for inducing the cell death, and a method for inducing the cell death.

All of the academic documents and the patent documents described in the present specification are incorporated by reference herein.

Example

Materials and Methods

1. Cell Culture

Used in the experiment was human cell cancer lines (ovary cancer cells (TYK-nu.CP-r cells (hereinafter referred to as TYK cells), stomach cancer cells (MKN28 cells), breast cancer cells (ZR-75 cells and SKBr3 cells), esophagus cancer cells (TE10 cells), pancreas cancer cells (MiaPaCa2 cells), colon cancer cells (SW480 cells and cervical cancer cells (HelaAG cells)), and human fibrosarcoma cell lines (HT-1080 cells). TE10 cells and SW480 cells were cultured in an RPMI-1640 medium complemented by 10% fetal bovine serum (FBS). Other cell lines were cultured in a Dulbecco's modified Eagle's medium (DMEM) including 10% FBS.

2. Vector Construction

Constructed was pcDNA3.1(+) (Invitrogen, Carlsbad, Calif., USA) including either one of four isoforms of human WT1 so as to be used for expressing the WT1 isoforms in a TYK cell. Each sequence of the WT1 isoforms, cloned in a pUC19 vector, was amplified by PCR using Pfx Taq polymerase (Invitrogen), and then inserted to a pEGFP vector (Clontech, PaloAlto, Calif., USA) so as to be used for a transient expression of a green fluorescent protein (GFP)-tagged WT1 isoform. It was determined by a direct sequencing method using BigDye Terminator V1.1 cycle sequencing kit (Applied Biosystems, Branchberg, NI, USA) that all of the sequences amplified by PCR did not have any mutation.

In order to prepare vectors for expressing α-actinin and cofilin, cDNA was prepared from mRNA isolated from a TYK cell, and then sequences of genes encoding α-actinin and cofilin were amplified by PCR with Pfx Taq polymerase. The sequences encoding α-actinin and cofilin were inserted to a pcDNA3.1/Zeo(+) vector (Invitrogen).

In order to prepare a siRNA vector targeting gelsolin, a pair of DNA sequences targeting a sequence of gelsolin mRNA (5'-UCCAGGAUGAAGCAGUCGCCAUUGUUGAA-3': SEQ ID NO:25) was synthesized (Japan BioScience, Saitama, Japan) and annealed, and then inserted to piGENE tRNA Pur (Clontech), which is a tRNA-shRNA expression vector.

3. Constitutive Expression of Vector

A mammalian expression vector and a siRNA vector targeting gelsolin were linearized by PvuI, and then transduced into cells by electroporation using Gene Pulsor II (Bio-Rad, Calif., USA). Cell clones that stably express the siRNA vector were isolated by using a suitable antibiotic for selection.

[Transient Expression of Vector]

By using Fugene 6 (Roche, Indianapolis, Ind., USA) in accordance with an instruction provided by the manufacturer, vector DNA (2 μg) was transfected into cells at a cell density of 5×10⁴ cells/ml. The cells transfected with the vector DNA were collected at the indicated time so as to be subjected to analysis.

[Reverse Transcription-PCR]

Total RNA was isolated by using ISOGEN (Nippon Gene, Tokyo, Japan), and then dissolved in diethylpyrocarbonate (DEPC)-treated water. The total RNA (2 μg) was converted into cDNA by using Moloney murine leukemia virus reverse transcriptase (Promega, Madison, Wis., USA).

Primer sequences and amplification conditions for subjecting eleven actin-binding proteins (including gelsolin, profilin, p125$^{fak}$, paxillin, α-actinin 1, VASP, and glyceraldehydes-3-phosphate dehydrogenase (GAPDH, used as a control)) to PCR were designed according to Salazar R. et al., Exp Cell Res; 249: 22-32 (1999). Primer sequences for PCR of talin, cofilin, ezrin, radixin, and moesin were shown in Table 1. The PCR products were separated on 2% agarose gel including ethidium bromide, and then visualized by UV light.

with antibodies specific to WT1 (Dakocytomation, Carpinteria, Calif., USA), GAPDH, actin (Chemicon, Temecula, Calif., USA), F-actin (Abcam, Cambridge, UK), α-tubulin, cofilin (Santa Cruz Biotechnology, Santa Cruz, Calif., USA), gelsolin (Sigma, St Louis, Mo., USA), and α-actinin 1 (clone AT6/172; Upstate Cell Signaling Solutions, New York, N.Y., USA), respectively.

6. Immunohistochemistry

Almost-confluent cells were collected and plated at a cell density of 5×10⁴ cells/ml in 1 ml of DMEM including 10% FBS, which is provided on sterilized cover glass (24×24 mm) placed in each well of a 6-well plate. After being incubated overnight, the cells on the cover glass were air-dried, and then fixed with paraformaldehyde (0.5% (for staining actin stress

TABLE 1

| | PRIMER SEQUENCE (SENSE) | PRIMER SEQUENCE (ANTISENSE) |
|---|---|---|
| GELSOLIN | CTT TCC AGC CAT ATC GCC ACC (SEQ ID NO: 1) | TTC TCT GCC TCG CTG GCT C (SEQ ID NO: 2) |
| PROFILIN | GGC CAG AAA TGT TCG GTG (SEQ ID NO: 3) | ACG GGA GGG ATA TGG GTA (SEQ ID NO: 4) |
| p125fak | GAC TCA CCT GGG TAC TGG TAT G (SEQ ID NO: 5) | ATC GCT CTT CAC CTG TTG ATA G (SEQ ID NO: 6) |
| PAXILLIN | CAG TCG CCA AAG GAG TCT G (SEQ ID NO: 7) | GTA GTC CTT GCG ACA GTA GGC (SEQ ID NO: 8) |
| α-ACTININ 1 | GGA GCC GAA GAA ATC GTG (SEQ ID NO: 9) | CTG CTC GTT CTC CTG GTT G (SEQ ID NO: 10) |
| VASP | GGA AAG TCA GCA AGC AGG (SEQ ID NO: 11) | TGT GCG GAA AGG AGA AGC (SEQ ID NO: 12) |
| TALIN | TGG CTA CCT GGA ACT GCT GGA C (SEQ ID NO: 13) | TCC AGC TCT CGT TCC TTC CGA AG (SEQ ID NO: 14) |
| COFILIN | AGT CTT CAA CGC CAG AGG AGG TG (SEQ ID NO: 15) | GTG CAG CGG TCC TTG ACC TCC T (SEQ ID NO: 16) |
| EZRIN | AGG AGT TGA TGC TGC GGC TGC A (SEQ ID NO: 17) | GTG GAT GAT GTC ATT GTG GGT C (SEQ ID NO: 18) |
| RADIXIN | ACC ACC AGT CAT TCC TCC AAC AG (SEQ ID NO: 19) | GGC AAG GTG GGA TGC ATT CCA TC (SEQ ID NO: 20) |
| MOESIN | TGG TGC CTT CAA GAC CTT CAC C (SEQ ID NO: 21) | GTC ACC TGA GAG GGT TGA GTA AAC (SEQ ID NO: 22) |
| GAPDH | GCC AAA AGG GTC ATC ATC TC (SEQ ID NO: 23) | GTA GAG GCA GGG ATG ATG TTC (SEQ ID NO: 24) |

With the pairs of primers above, mRNAs of the actin-binding proteins were amplified by reverse transcription-PCR (20 cycles, with an annealing temperature of 60° C.).

5. Western Blotting

Cells were washed two times with phosphate-buffered saline (PBS), and then dissolved in SDS sample buffer (including 0.125M Tris-HCl (pH6.8), 100 mM dithiothreitol, 4% SDS, 10% sucrose, and 0.004% bromophenol blue). Cell lysate was subjected to SDS-PAGE, and transferred to Immobilon polyvinylidene difluoride membrane (Millipore, Bedford, Mass., USA). Then, the cell lysate was immunoblotted fiber), or 4% (for staining other proteins)). Then, the cells were washed two times with PBS including 0.05% Tween 20, and thereafter made to be permeable by using PBS including 1% Triton X-100 (leaving for 10 minutes). The cells were incubated for 30 minutes in blocking buffer (PBS including 2% BSA, 0.2% Tween 20, 6.7% glycerin, and 0.1% NaN₃), and then immunoblotted with a primary antibody specific to gelsolin, α-actinin 1, or cofilin by reacting for one hour. After being washed with PBS including 0.05% Tween 20, the cells were incubated for one hour with a secondary antibody which corresponds to the primary antibody. Then actin stress fiber and vinculin (focal adhesion protein) were stained with FAK100 staining kit (Chemicon) according to an instruction provided by the manufacturer. Expressions of these proteins were analyzed by using a confocal microscope (LSM510 ver2.8; Carl Zeiss, Germany).

7. Cell Attachment Assay and Cell Detachment Assay

A cell attachment assay was carried out according to Yu D. H. et al., J. Biol. Chem. 273: 21 125-131 (1998). Serum depletion in DMEM including 0.5% FBS was carried out overnight. Cells ($1\times10^4$ cells) were plated at a cell density of $1\times10^4$ cells/well in 100 µl of the serum-free DMEM provided in a 96-well plate that is coated with fibronectin (Sigma) at a concentration of 10 µg/ml, and then incubated at 37° C. for 30 minutes under the presence of 5% $CO_2$. After being washed two times with PBS, cells attached to the well were treated with trypsin, and then the number of the cell was counted.

A cell detachment assay was carried out according to Grille S. J. et al., Cancer Res. 63: 2172-8 (2003). Cells were plated in 1 ml of DMEM including 10% FBS, which was provided in a 24-well plate, and then incubated overnight so as to be attached to the well. Next, the cells were treated with 0.25% trypsin (Tacalai Tesque, Kyoto, Japan) at room temperature, and then collected 2 minutes after the trypsin treatment.

8. Analysis of Individual Cell Movement

An individual cell movement was observed by using a time-lapse microscope. In summary, cells were plated on a 35 mm dish at 30% confluency, and thereafter incubated for 48 hours. Then, the cells were incubated at 37° C. under the presence of 5% $O_2$, 5% $CO_2$, and 90% $N_2$, and observed for 5 hours at intervals of 2 minutes by using Meta cam software (Universal Imaging Software, Buckinghamshire, UK). Positions ([X, Y]) of the cells, traced at a certain point of time, were determined by using Commotion Pro 4.0 software (Pinnacle Systems, Calif., USA) so that distances that the cell moved in every 2 minutes were calculated. Velocity (µm/h) of the movements of the cell that was traced was determined from a total distance of 5-hour movement.

9. Wound-Healing Assay

A wound-healing assay was carried out according to Stahle M. et al., J. Cell. Sci.; 116: 3835-46 (2003). In summary, cell suspension ($2\times10^5$ cells/2 ml) was plated at a cell density of $1\times10^5$ cells/ml in 2 ml of DMEM including 10% FBS, which was provided in a 6-well plate, so as to grow until confluent. Then, a confluent cell monolayer was scratched with a yellow chip so that the scratched cells were detached. The remained cell monolayer was washed two times moderately with serum-free DMEM, and then incubated in DMEM including 10% FBS. Pictures of a site where the cells were detached were taken at the time of scratching and 12 hours after scratching. Cell migration was found as an average ratio (percent) of length of protrusion to length of the scratch at three different sites in several sights in a same picture.

10. Transwell Migration Assay

A chemotaxis invasion assay was carried out according to Yoshioka K. et al., Proc Natl Acad Sci USA; 100, 7247-52 (2003). After being incubated for 2 hours in serum-free DMEM including 0.1% BSA, cells ($3\times10^4$ cells) in 20 µl of serum-free DMEM including 0.1% BSA were applied to Transwell upper chamber (PET membrane 8 µm pore size; BD Falcon, N.J., USA). Lower chamber was filled with 5%-serum DMEM including 0.1% BSA. After 18 hours, cells that had moved to the underside of the PET membrane and the bottom surface of a well were immobilized with 70% methanol, and the number thereof was counted.

11. Transducing shRNA In Vivo

Human tumor cells HT-1080 ($5\times10^6$ cells) expressing WT1 were suspended in 100 µl of PBS. The suspension was mixed with 50 µl of matrigel (BD), and then transplanted subcutaneously in a ventral side of a 6-week-old female Balb/c nu/nu mouse. From 3 days after the transplanting, WT1-shRNA (50 µg) targeting WT1 17AA(−) isoform, or shRNA control vector (50 µg) was administered, twice a week under anesthesia, to the site where the tumor cells were transplanted. Major axis and minor axis of a tumor mass at the site where the tumor cells were transplanted were measured 2 weeks after the transplantation. The volume of the tumor mass was defined as (major axis)×(minor axis)×(minor axis)/2.

12. Statistical Analysis

A statistically significant difference among averages of test groups was evaluated by using an unpaired t-test.

13. Description of Drawings

Figure 1B:
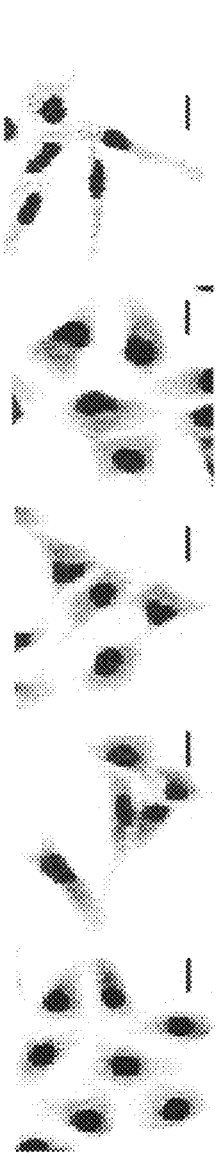
FIG. 1(b) is a view showing a morphological change of TYK ovary cancer cell induced by a constitutive expression of WT1 17AA(−)/KTS(−) isoform.
Figure 1C:
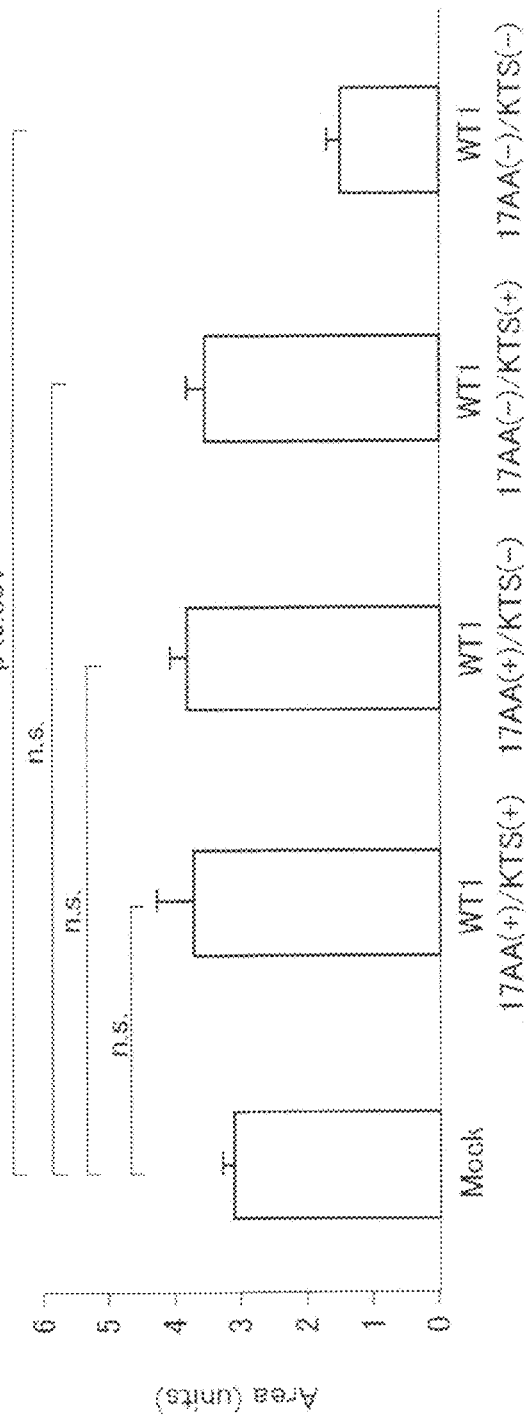
FIG. 1(c) is a view showing a morphological change of TYK ovary cancer cell induced by a constitutive expression of WT1 17AA(−)/KTS(−) isoform.

FIG. 1 are views showing a morphological change of TYK ovary cancer cell induced by a constitutive expression of WT1 17AA(−)/KTS(−) isoform. FIG. 1(a) shows, as an example, results of Western blotting showing the presence or absence of expressions of WT1 proteins in four TYK cell lines (each being transduced with one of four different WT1 isoforms). FIG. 1(b) shows, as an example, a change in cell morphology caused by stable expressions of each WT1 isoform in the TYK cell. FIG. 1(c) shows averages of relative areas of eight or more individual cells obtained from three cell clones. The areas were calculated by using NIH Image Software.

FIG. 2 are views showing a morphological change of various types of cancer cells induced by a constitutive expression of WT1 17AA(−)/KTS(−) isoform. FIG. 2(a) is a view showing various types of cancer cells (ZR-75, HT-1080, MKN28, SKBr3, and TE10, for example) in which GFP-tagged WT1 17AA(−)/KTS(−) isoform was transiently expressed. The cells were morphologically analyzed by using a confocal microscope 48 to 72 hours after transfection. The upper panels are transmitted-light images; and the lower panels are fluorescent images. The arrows indicate cells expressing GFP-tagged WT1 17AA(−)/KTS(−) isoform. Scale bars are 10 µm long. FIG. 2(b) is a view showing averages of relative areas of more than 9 individual cells. The areas were calculated by using NIH Image Software.

Figure 3:
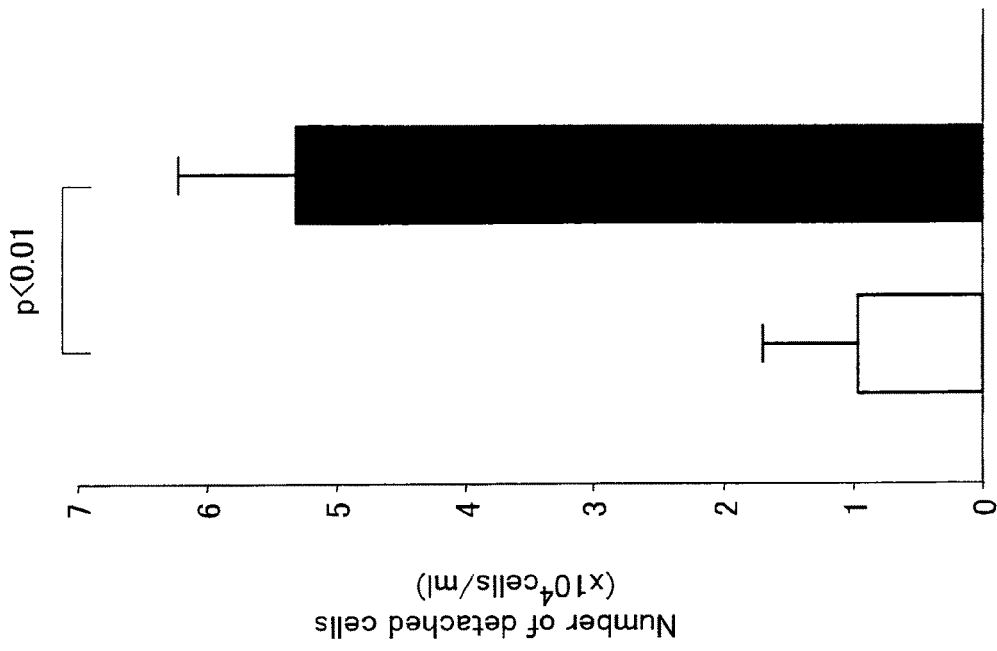
FIG. 3(a) is a view showing a suppression of cell-substratum adhesion induced by a stable expression of WT1 17AA(−)/KTS(−) isoform. TYK cells transduced with the WT1 17AA(−)/KTS(−) isoform and TYK cells transduced with a control vector were analyzed in regard to the cell-substratum adhesion by using a cell attachment assay.
FIG. 3(b) is a view showing a suppression of cell-substratum adhesion induced by a stable expression of WT1 17AA(−)/KTS(−) isoform. TYK cells transduced with the WT1 17AA(−)/KTS(−) isoform and TYK cells transduced with a control vector were analyzed in regard to strength of the cell-substratum adhesion by using a cell detachment assay.
Figure 3:
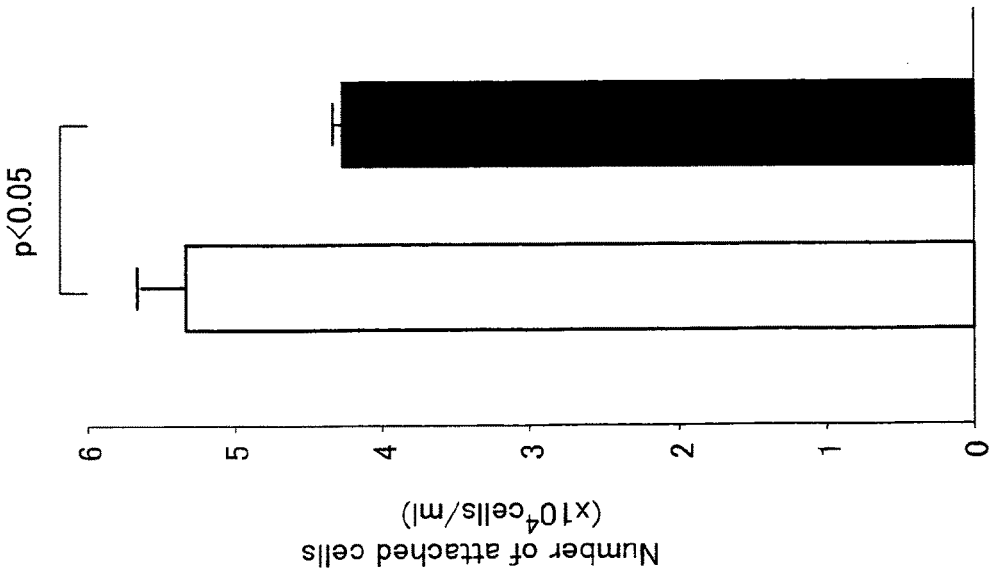

FIG. 3 are views showing a suppression of cell-substratum adhesion induced by a stable expression of WT1 17AA(−)/KTS(−) isoform. The average number of TYK cell clones transduced with the WT1 17AA(−)/KTS(−) isoform is represented by (■). The average number of cell clones transduced with a control vector is represented by (□). Each cell clone was separately applied to the experiment three times. In FIG. 3(a), TYK cells transduced with the WT1 17AA(−)/KTS(−) isoform and TYK cells transduced with the control vector were analyzed in regard to the cell-substratum adhesion by using a cell attachment assay. In FIG. 3(b), TYK cells transduced with the WT1 17AA(−)/KTS(−) isoform and TYK cells transduced with a control vector were analyzed in regard to strength of the cell-substratum adhesion by using a cell detachment assay.

FIG. 4 are views showing an enhancement of cell movement induced by a constitutive expression of WT1 17AA(−)/KTS(−) isoform. In FIG. 4(a), movements of individual TYK cells expressing GFP-WT1 17AA(−)/KTS(−) isoform and individual TYK cells not expressing the GFP-WT1 17AA(−)KTS(−) isoform were recorded for 5 hours at intervals of 2 minutes by using a Time-lapse video recorder. Velocity of the movements of the cells was calculated. The average velocity of the cells expressing the GFP-WT1 17AA(−)/KTS(−) isoform is represented by (■). The average velocity of the cells not expressing the GFP-WT1 17AA(−)KTS(−) isoform is represented by (□). The experiment was separately carried out ten times. In FIG. 4(b), TYK cells (■) transduced with a WT1 17AA(−)/KTS(−) isoform expression vector and TYK cells (□) transduced with a control vector were analyzed in regard to collective migration by using a wound-healing assay. Each cell clone was separately applied to the experiment three times. The cell migration was found as an average ratio (percent) of length of a protrusion to width of cell detachment carried out firstly by a chip at three different sites. Scale bars are 50 µm long. In FIG. 4(c), TYK cells (■) transduced with a WT1 17AA(−)/KTS(−) isoform expression vector and TYK cells (□) transduced with a control vector were analyzed in regard to chemotaxis toward Delbucco's modified Eagle's medium including 5% FBS by using a Transwell Migration assay. Each cell clone was separately applied to the experiment three times. Cells that moved from an upper chamber into a lower chamber were stained with MayGrunwald-Giemsa, and the number thereof was counted. Scale bars are 50 µm long.

FIG. 5 are views showing a change of expressions of filamentous actin (F-actin) and actin-binding proteins (ABP) induced by a constitutive expression of WT1 17AA(−)/KTS(−) isoform. FIG. 5(a) shows results of immunohistochemical staining for F-actin, vinculin (focal adhesion protein), and nuclei in a TYK cell transduced with the WT1 17AA(−)/KTS(−) isoform and a TYK cell transduced with a control vector. Scale bars are 10 µm long. In FIG. 5(b), lysate (lanes 1 and 2) of individual cells transduced with a control vector and lysate (lanes 3 and 4) of individual cells transduced with the WT1 17AA(−)/KTS(−) isoform were immunoblotted with antibodies specific to total actin, F-actin, α-tubulin, and GAPH, respectively. Scale bars are 10 µm long. In FIG. 5(c), expressions of mRNA in individually-isolated TYK cell clones (n=3, lanes 1 through 3) transduced with a control vector and in individually-isolated TYK cell clones (n=3, lanes 4 through 6) transduced with the WT1 17AA(−)/KTS(−) isoform were analyzed by RT-PCR under a condition described in Table 1. Scale bars are 10 µm long. In FIG. 5(d), TYK cell clones (lanes 1 and 2) transduced with a control vector and TYK cell clones (lanes 3 and 4) transduced with the WT1 17AA(−)/KTS(−) isoform were immunoblotted with antibodies specific to α-actinin 1, cofilin, and gelsolin, respectively. In FIG. 5(e), immunohistochemical staining for α-acinin 1, cofilin, and gelsolin in TYK cells transduced with the WT1 17AA(−)/KTS(−) isoform or with a control vector was carried out. At the same time, cell nuclei were stained with propidium iodide. Scale bars are 10 µm long.

Figure 5A:
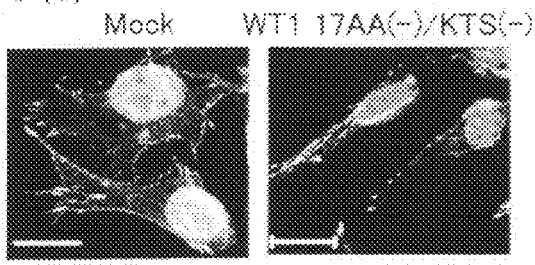
FIG. 5(a) is a view showing a change of expressions of filamentous actin (F-actin) and actin-binding proteins (ABP) induced by a constitutive expression of WT1 17AA(−)/KTS(−) isoform.
Figure 5F:
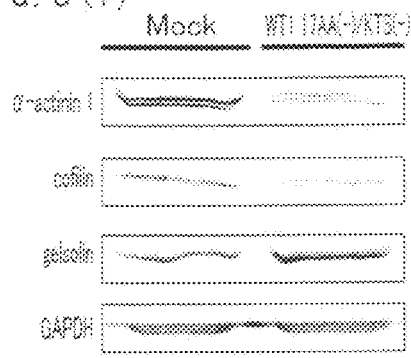
FIG. 5(f) is a view showing a change of expressions of fibrous actin (F-actin) and actin-binding proteins (ABP) induced by a constitutive expression of WT1 17AA(−)/KTS (−) isoform. HT-1080 cell clones transduced with a control vector or with the WT1 17AA(−)/KTS(−) isoform were immunoblotted with antibodies specific to α-acinin 1, cofilin, and gelsolin, respectively.
Figure 5B:
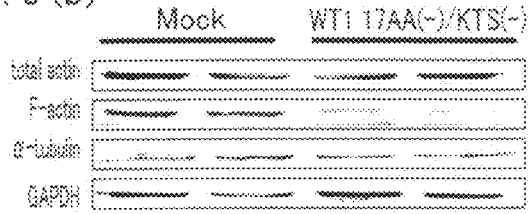
FIG. 5(b) is a view showing a change of expressions of fibrous actin (F-actin) and actin-binding proteins (ABP) induced by a constitutive expression of WT1 17AA(−)/KTS(−) isoform. Lysate (lanes 1 and 2) of individual cells transduced with a control vector and lysate (lanes 3 and 4) of individual cells transduced with the WT1 17AA(−)/KTS(−) isoform were immunoblotted with antibodies specific to total actin, F-actin, α-tubulin, and GAPH, respectively.
Figure 5C:
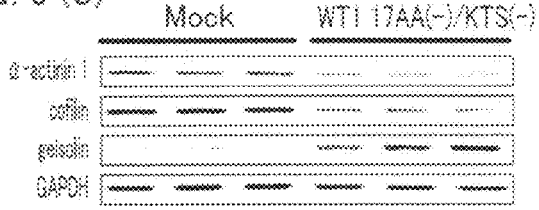
FIG. 5(c) is a view showing a change of expressions of fibrous actin (F-actin) and actin-binding proteins (ABP) induced by a constitutive expression of WT1 17AA(−)/KTS(−) isoform. Expressions of mRNA in individually-isolated TYK cell clones (n=3, lanes 1 through 3) transduced with a control vector and in individually-isolated TYK cell clones (n=3, lanes 4 through 6) transduced with the WT1 17AA(−)/KTS(−) isoform were analyzed by RT-PCR under a condition described in Table 1.
Figure 5G:
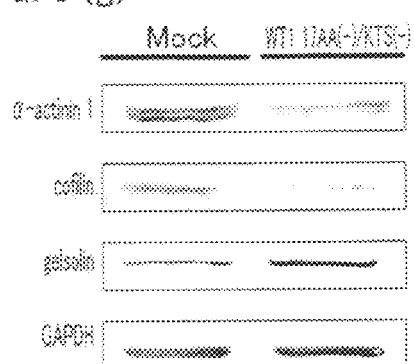
FIG. 5(g) is a view showing a change of expressions of fibrous actin (F-actin) and actin-binding proteins (ABP) induced by a constitutive expression of WT1 17AA(−)/KTS(−) isoform. TE10 cell clones transduced with a control vector or with the WT1 17AA(−)/KTS(−) isoform were immunoblotted with antibodies specific to α-acinin 1, cofilin, and gelsolin, respectively.
Figure 5D:
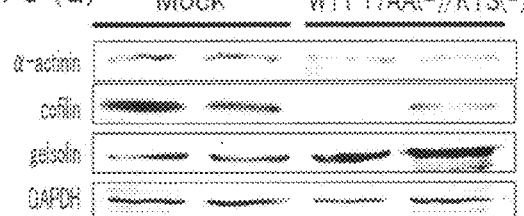
FIG. 5(d) is a view showing a change of expressions of fibrous actin (F-actin) and actin-binding proteins (ABP) induced by a constitutive expression of WT1 17AA(−)/KTS(−) isoform. TYK cell clones (lanes 1 and 2) transduced with a control vector and TYK cell clones (lanes 3 and 4) transduced with the WT1 17AA(−)/KTS(−) isoform were immunoblotted with antibodies specific to α-actinin 1, cofilin, and gelsolin, respectively.
Figure 5E:
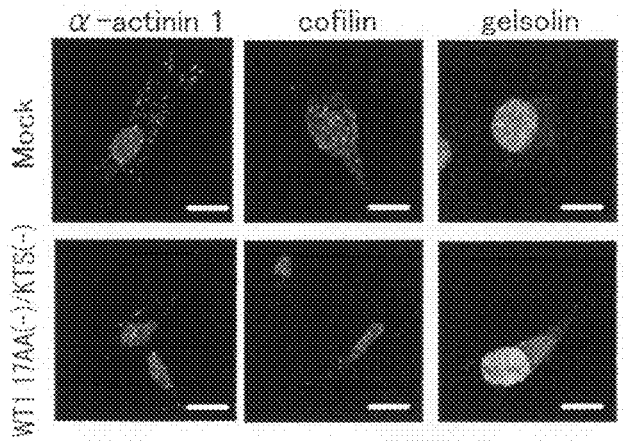
FIG. 5(e) is a view showing a change of expressions of fibrous actin (F-actin) and actin-binding proteins (ABP) induced by a constitutive expression of WT1 17AA(−)/KTS(−) isoform. Immunohistochemical staining for α-acinin 1, cofilin, and gelsolin in TYK cells transduced with the WT1 17AA(−)/KTS(−) isoform or with a control vector was carried out. At the same time, cell nuclei were stained with propidium iodide.
Figure 6A:
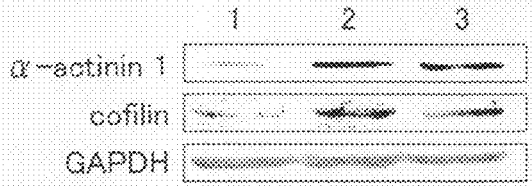
FIG. 6(a) is a view showing that a phenotype of a TYK cell in which stable expressions of α-actinin and cofilin were induced by transducing WT1 17AA(−)/KTS(−) isoform was restored in a phenotype of its parent TYK cell. An α-actinin expression vector and a cofiline expression vector (TW/ACTN-CFL) or a control vector were co-transfected into TYK cells transduced with the WT1 17AA(−)/KTS(−) isoform.
Figure 6B:
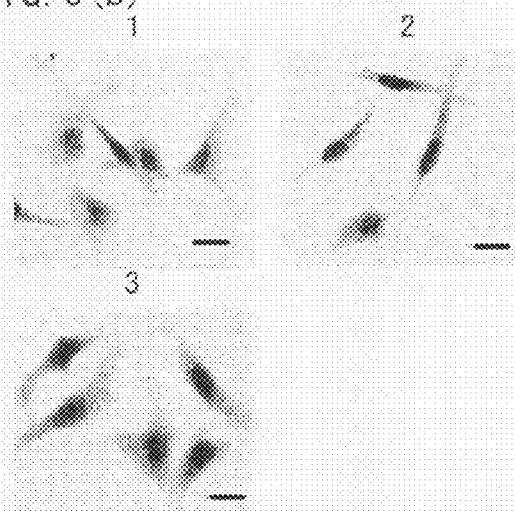
FIG. 6(b) is a view showing that a phenotype of a TYK cell in which stable expressions of α-actinin and cofilin were induced by transducing WT1 17AA(−)/KTS(−) isoform was restored in a phenotype of its parent TYK cell. An α-actinin expression vector and a cofiline expression vector (TW/ACTN-CFL) or a control vector were co-transfected into TYK cells transduced with the WT1 17AA(−)/KTS(−) isoform.
Figure 6C:
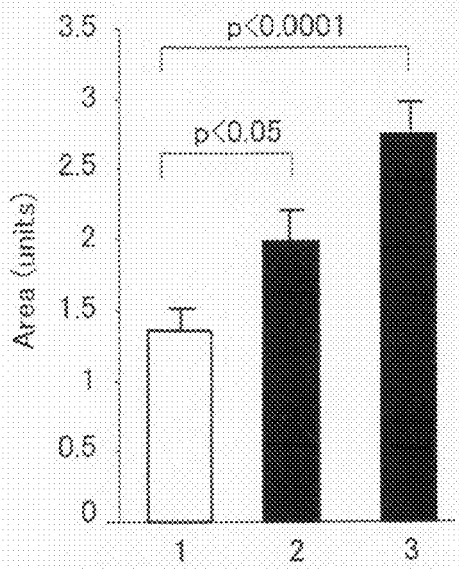
FIG. 6(c) is a view showing that a phenotype of a TYK cell in which stable expressions of α-actinin and cofilin were induced by transducing WT1 17AA(−)/KTS(−) isoform was restored in a phenotype of its parent TYK cell. An α-actinin expression vector and a cofiline expression vector (TW/ACTN-CFL) or a control vector were co-transfected into TYK cells transduced with the WT1 17AA(−)/KTS(−) isoform.
Figure 6D:
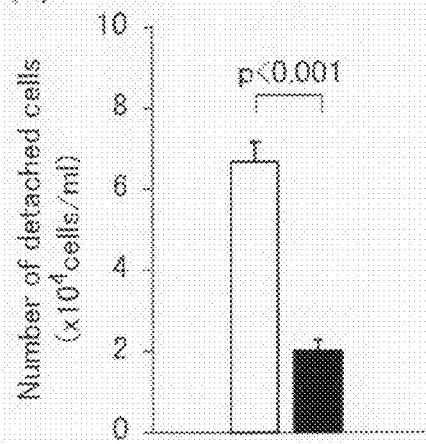
FIG. 6(d) is a view showing that a phenotype of a TYK cell in which stable expressions of α-actinin and cofilin were induced by transducing WT1 17AA(−)/KTS(−) isoform was restored in a phenotype of its parent TYK cell. An α-actinin expression vector and a cofiline expression vector (TW/ACTN-CFL) or a control vector were co-transfected into TYK cells transduced with the WT1 17AA(−)/KTS(−) isoform.
Figure 6E:
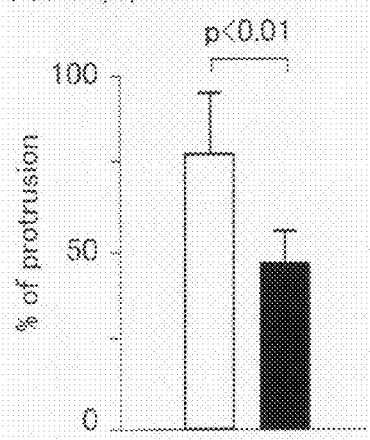
FIG. 6(e) is a view showing that a phenotype of a TYK cell in which stable expressions of α-actinin and cofilin were induced by transducing WT1 17AA(−)/KTS(−) isoform was restored in a phenotype of its parent TYK cell. An α-actinin expression vector and a cofiline expression vector (TW/ACTN-CFL) or a control vector were co-transfected into TYK cells transduced with the WT1 17AA(−)/KTS(−) isoform.
Figure 6F:
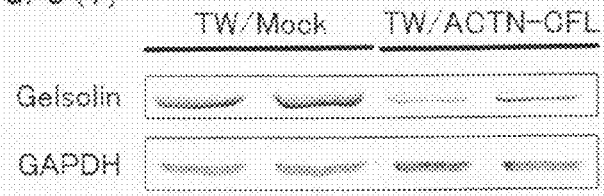
FIG. 6(f) is a view showing that a phenotype of a TYK cell in which stable expressions of α-actinin and cofilin were induced by transducing WT1 17AA(−)/KTS(−) isoform was restored in a phenotype of its parent TYK cell. An α-actinin expression vector and a cofiline expression vector (TW/ACTN-CFL) or a control vector were co-transfected into TYK cell transduced with the WT1 17AA(−)/KTS(−) isoform.

In FIG. 5(f), HT-1080 cell clones transduced with a control vector or with the WT1 17AA(−)/KTS(−) isoform were immunoblotted with antibodies specific to α-acinin 1, cofilin, and gelsolin, respectively. In FIG. 5(g), TE10 cell clones transduced with a control vector or with the WT1 17AA(−)/KTS(−) isoform were immunoblotted with antibodies specific to α-acinin 1, cofilin, and gelsolin, respectively.

FIG. 6 are views showing that a phenotype of a TYK cell in which stable expressions of α-actinin and cofilin are induced by transducing WT1 17AA(−)/KTS(−) isoform is restored in a phenotype of its parent TYK cell. An α-actinin expression vector and a cofiline expression vector (TW/ACTN-CFL) or a control vector were co-transfected into TYK cells transduced with the WT1 17AA(−)/KTS(−) isoform. FIG. 6(a) shows expression levels of α-actinin and cofilin, which were determined by Western blotting. FIG. 6(b) shows the cells stained with May Grunwald-Giemsa. FIG. 6(c) shows cell areas calculated by NIH Image software (1: TW/Mock cell clone; 2 and 3: different TW/ACTN-CFL cell clones, respectively). Scale bars are 10 µm long. The results of TW/ACTN-CFL cells are represented by (■); and the result of TW/Mock cells is represented by (□). FIG. 6(d) shows a cell-substratum adhesion determined by a detachment assay. The result of TW/ACTN-CFL cells is represented by (■); and the result of TW/Mock cells is represented by (□). FIG. 6(e) shows a collective cell migration analyzed by a wound-healing assay. The cell migration is represented as an average of the ratio (percentage) of length of protrusion to width of first detachment of cells at three different sites. The result of TW/ACTN-CFL cells is represented by (■); and the result of TW/Mock cells is represented by (□). FIG. 6(f) shows an expression level of gelsolin, which was determined by Western blotting.

FIG. 7 are views showing that a suppression of gelsolin expression reduced a cell migration, however, did not affect cell morphology or a cell-substratum adhesion. A gelsolin-specific siRNA vector (TW/GSNsiRNA) or a control vector (TW/siMock) was transduced into TYK cells transduced with WT1 17AA(−)/KTS(−) isoform. FIG. 7(a) shows an expression level of gelsolin protein, which was determined by Western blotting. Three different cell clones were applied to the experiment. FIG. 7(b) shows the cells stained with May Grunwald-Giemsa. Scale bars are 10 µm long. FIG. 7(c) shows the areas of the TW/Mock cell clones and the TW/GSNsiRNA cell clones, which were calculated by NIH Image software. The result of the cell clones transduced with the gelsolin-specific siRNA vector is represented by (■); and the result of the cell clones transduced with the Mock siRNA vector is represented by (□). FIG. 7(d) shows a cell-substratum adhesion determined by a detachment assay. The result of the cell clones transduced with the gelsolin-specific siRNA vector is represented by (■); and the result of the cell clones transduced with the Mock siRNA vector is represented by (□). FIG. 7(e) shows a collective cell movement analyzed by a wound-healing assay. The result of cell clones transduced with the gelsolin-specific siRNA vector is represented by (■); and the result of the cell clones transduced with the Mock siRNA vector is represented by (□). FIG. 7(f) shows expression levels of □-actinin 1 and cofilin, which were determined by Western blotting.

Figure 8:
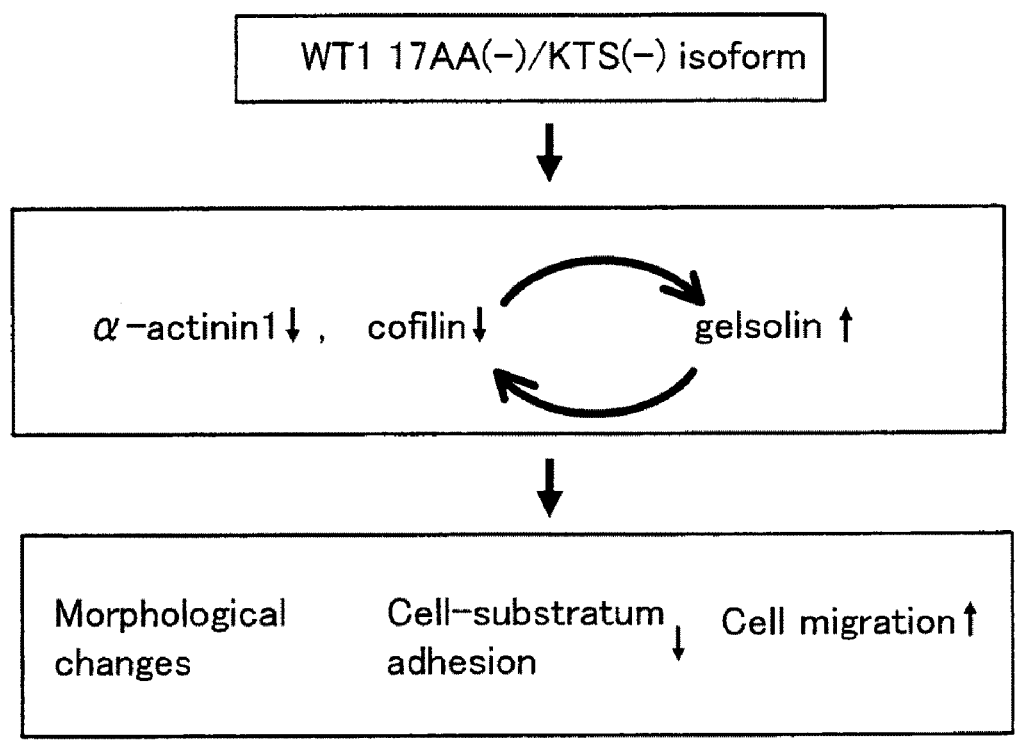
FIG. 8 is a view showing a possibility of function of WT1 17AA(−)/KTS(−) isoform in controlling of cytoskeletal dynamics.

FIG. 8 is a view showing a possibility of function of WT1 17AA(−)/KTS(−) isoform in controlling cytoskeletal dynamics. A constitutive expression of the WT1 17AA(−)/KTS(−) isoform performs a down-regulation of both expressions of □-actinin 1 and cofilin, and a up-regulation of an expression of gelsoline. Moreover, □-actinin 1/cofilin and gelsolin are mutually regulated in the downstream signaling of the WT1 17AA(−)/KTS(−) isoform. That is to say, functions of the WT1 17AA(−)/KTS(−) isoform (e.g., induction of morphological change in cell, weakening of cell-substratum adhesion, enhancement of cell movement) are wholly or partly performed via regulations of □-actinin 1/cofilin and gelsolin.

Example 1

Induction of Morphological Change in Various Types of Cancer Cells by Constitutive Expression of WT1 17AA(−)/KTS(−) Isoform In order to examine how a WT1 gene affects actions of a cancer cell, any one of four WT1 genes was stably expressed in TYK ovary cancer cells. Then, TYK cell clones in which the transduced WT1 isoform was highly expressed were isolated (FIG. 1(a)). In the TYK cell, a stable expression of the WT1 17AA(−)/KTS(−) isoform induced a morphological change characterized by a cell morphology having a small size and a fibroblast-like shape (FIGS. 1(b) and 1(c)). In contrast, stable expressions of WT1 isoforms other than the 17AA(−)/KTS(−) isoform did not induce any morphological change in the TYK cell.

Furthermore, in order to examine whether or not the WT1 17AA(−)/KTS(−) isoform induces a morphological change in various cancer cells other than the TYK cell, a GFP-tagged WT1 17AA(−)/KTS(−) isoform was transiently expressed in MKN28 cells, ZR-75 cells, SKBr3 cells, TE10 cells, MiaPaCa2 cells, SW480 cells, HelaAG cells, and HT-1080 cells (FIG. 2). Results of confocal microscopy indicated that the transient expression of the GFP-tagged WT1 17AA(−)/KTS(−) isoform induced a morphological change in the MKN28 cells, the ZR-75 cells, the SKBr3 cells, the TE10 cells, and the HT-1080 cells in terms of a cell size (being smaller) and a three-dimensional shape of the cells. On the other hand, an expression of a GFP control vector did not induce any morphological change in these cell lines. Rest of the three cell lines (MiaPaCa2 cell, SW480 cell, and HelaAG cell) did not clearly show any morphological change (data not shown).

In order to verify that only the WT1 17AA(−)/KTS(−) isoform can induce the morphological change in the cancer cell, any one of other three GFP-tagged WT1 isoforms was transiently expressed in HT-1080 cells and TE10 cells, whose morphological changes were induced by the WT1 17AA(−)/KTS(−)isoform. Results of confocal microscopy indicated that any of the three GFP-tagged WT1 isoforms did not induce a morphological change in the two cell lines (data not shown).

Example 2

Suppression of Cell-Substratum Adhesion by Constitutive Expression of WT1 17AA(−)/KTS(−) Isoform In order to examine whether or not a morphological change observed in a cell transduced with WT1 17AA(−)/KTS(−) isoform was attributed to a change in ability of the cell to spread, effects of a constitutive expression of the WT1 17AA(−)/KTS(−) isoform on cell-substratum adhesion was analyzed in regard to TYK cells. Results of a cell attachment assay indicated that, in cell clones (n=4) transduced with the WT1 17AA(−)/KTS(−) isoform, adhesion of the cells to substrate was significantly weakened compared to cell clones (n=4) transduced with a Mock vector (FIG. 3(a)). Moreover, results of a cell detachment assay indicated that, in cell clones (n=5) transduced with the WT1 17AA(−)/KTS(−) isoform, strength of cell-substratum adhesion was significantly reduced compared to cell clones (n=5) transduced with the Mock vector (FIG. 3(b)). In the cell detachment assay, 53.3% of the cells transduced with the WT1 17AA(−)/KTS(−) isoform was detached from a plastic substrate two minutes after a trypsin treatment. On the other hand, only 9.8% of the cells transduced with the control vector was detached from the substrate. That is to say, the strength of cell-substratum adhesion was reduced in the cell transduced with the WT1 17AA(−)/KTS(−) isoform, compared to the cell transduced with the control vector.

Example 3

Enhancement in Cell Movement by Constitutive Expression of WT1 17AA(−)/KTS(−) Isoform In order to examine how a constitutive expression of WT1 17AA(−)/KTS(−) isoform affects cell migration, cells transduced with the WT1 17AA(−)/KTS(−) isoform were analyzed in terms of individual migration, collective migration, and in vitro invasion.

Movements of individual TYK cell transduced with the WT1 17AA(−)/KTS(−) isoform were evaluated by using a time-lapse microscope (FIG. 4(a)). Migrations of the individual TYK cell were recorded at intervals of 2 minutes for 5 hours with (n=19) or without (n=19) a transient expression of GFP-WT1 17AA(−)/KTS(−) isoform in the cell. Then, the cell movements were traced so that velocities of the cell movement were calculated. Results of the experiment that was separately carried out 10 times indicated that random movement velocity of the TYK cells expressing the GFP-WT1 17AA(−)/KTS(−) isoform was increased by 1.8 times compared to the cells not expressing the GFP-WT1 17AA(−)/KTS(−) isoform. Meanwhile, migrations of the individual TYK cell expressing a GFP-mock vector did not significantly differ from those of cells not expressing the GFP-mock vector (data not shown).

In order to further clarify the enhancement in ability of the GFP-WT1 17AA(−)/KTS(−) isoform-transduced cells to move, a collective cell migration was analyzed by using a wound-healing assay (FIG. 4(b)). It was found out that the distance that the cell clones (n=4) transduced with the WT1 17AA(−)/KTS(−) isoform moved during 12 hours after the wound was increased by 1.8 times compared to cells (n=5) transduced with a Mock vector.

Further, in vitro invasion of the cell clones transduced with the WT1 17AA(−)/KTS(−) isoform was analyzed by using a Transwell Migration assay (FIG. 4(c)). The number of cells that penetrate a membrane to invade was counted 18 hours after plating the cells in an upper chamber. It was found out that chemotaxis of the cell clones (n=4) transduced with the WT1 17AA(−)/KTS(−) isoform toward FBS was enhanced by 8 times compared to that of the cells (n=5) transduced with the Mock vector.

Example 4

Change in Expression of Filamentous Actin and Actin-Binding Protein by Constitutive Expression of WT1 17AA(−)/KTS(−) Isoform In a TYK cell, a constitutive expression of WT1 17AA(−)/KTS(−) isoform induced a morphological change in the cell, and weakened a cell-substratum adhesion, and also enhanced a cell movement. Since these results are suggestive of a change in cytoskeletal structure, an analysis thereof was carried out on the basis of immunocytochemistry. As expected, in the TYK cells, a filamentous actin (F-actin) network was reduced, and moreover, desmosome was reduced (FIG. 5(a)). It was indicated by Western blotting that an expression level of F-actin was decreased in cells transduced with the WT1 17AA(−)/KTS(−) isoform compared to cells transduced with a Mock vector. On the other hand, total expression levels of actin and α-tubuline did not differ between the cells transduced with the WT1 17AA(−) isoform/KTS(−) isoform and the cells transduced with the Mock vector (FIG. 5(b)). In response to these results, expressions of mRNA encoding each of eleven actin-binding proteins (including α-actinin 1, cofilin, gelsolin, FAK, profilin, VASP, talin, ezrin, moesin, and radixin) in the cells transduced with the WT1 17AA(−)/KTS(−) isoform were analyzed by using RT-PCR. As shown in FIG. 5(c), in the cells transduced with the WT1 17AA(−)/KTS(−) isoform, expressions of α-actinin 1 and cofilin were suppressed, and an expression of gelsolin was increased. The decreased expressions of α-actinin 1 and cofilin in addition to the increased expression of gelsolin were confirmed at the protein level by Western blotting (FIG. 5(d)). It was indicated by immunocytochemistry that, in cytoplasm of the cells transduced with the WT1 17AA(−)/KTS(−) isoform, expressions of α-actinin 1 protein and cofilin protein were suppressed, and an expression of gelsolin protein was increased (FIG. 5(e)). Expressions of mRNA encoding rest of the eight actin-binding proteins did not differ between the cells transduced with the WT1 17AA(−)/KTS(−) isoform and the cells transduced with the Mock vector (data not shown).

Further, in order to confirm that the WT1 17AA(−)/KTS(−) isoform regulates expressions of gelsolin, α-actinin 1, and cofilin, the WT1 17AA(−)/KTS(−) isoform was stably expressed in a HT-1080 cell and a TE10 cell. As a result of Western blotting, it was indicated that, although the expressions of α-actinin 1 and cofilin were decreased, the expression of gelsolin was increased in the cell transduced with the WT1 17AA(−)/KTS(−) isoform compared to a cell transduced with a control pcDNA 3.1/Zeo(+) vector (FIGS. 5(f) and 5(g)).

Example 5

Restoration of Phenotype of WT-1 17AA(−)/KTS(−) Isoform-Transduced Cells by Constitutive Expressions of Both of α-Actinin 1 and Cofilin or by Suppression of Gelsolin with Gelsolin-Specific siRNA In order to determine whether or not a decrease in expressions of α-actinin 1 and cofilin causes, in a TYK cell transduced with WT1 17AA(−)/KTS(−) isoform, a morphological change, a reduction in desmosome, and an enhancement in cell migration, an α-actinin 1/pcDNA3.1/Zeo(+) vector and a cofilin/pcDNA3.1/Z(+) vector were co-transduced into TYK cells transduced with the WT1 17AA(−)/KTS(−) isoform. Then, cell clones (TW/ACTN-CFL cell) in which α-actinin 1 and cofilin were expressed to a same extent as in a parent TYK cell were isolated (FIG. 6(a)). Characteristics of the TW/ACTN-CFL cells were compared to those of TYK cells (TW/Mock) transduced with the WT1 17AA(−)/KTS(−) isoform and with a control pcDNA3.1/Zeo(+) vector. As a result, the TW/ACTN-CFL cells displayed morphological changes to a well-spreading cell shape like the parent TYK cell. On the other hand, the TW/Mock cells were not changed in shape (FIGS. 6(b) and 6(c)). It was shown by a cell detachment assay that the number of detached cells in the TW/ACTN-CFL cell clones (n=3) two minutes after a trypsin treatment decreased compared to the number thereof in the TW/Mock cells (n=3) so as to be similar to the number thereof in the parent TYK cells (FIG. 6(d)). Further, it was shown by a wound-healing assay that a cell movement of the TW/ACTN-CFL cell clones (n=3) was reduced compared to that of the TW/Mock cell clones (n=3) so as to be similar to that of the parent TYK cells (FIG. 6(e)). In contrast, TYK cells transduced with the WT1 17AA(−)/KTS(−) isoform, in which either one of cofilin and α-actinin 1 was constitutively expressed, did not exhibit same characteristics as the parent TYK cells (data not shown). This shows that α-actinin 1 and cofilin act in corporation on regulation of the shape and action of the TYK cells.

In order to determine whether or not an increase in expression level of gelsolin affects the morphological change, the weakened cell-substratum adhesion, and the enhanced cell movement in TYK cells transduced with the WT1 17AA(−)/KTS(−) isoform, a gelsolin-specific siRNA vector or a Mock vector was transduced into the WT1 17AA(−)/KTS(−) isoform-transduced TYK cells. Then, cell clones in which gelsolin was expressed to a same extent as in parent TYK cells were isolated (TW/GSNsiRNA) (n=3) (FIG. 7(a)). The WT1 17AA(−)/KTS(−) isoform-transduced TYK cells in which an expression of gelsolin was suppressed by the gelsolin-specific siRNA vector did not induce any morphological changes in TYK cells transduced with the WT1 17AA(−)/KTS(−) isoform and with a Mock siRNA vector (TW/siMock) (n=3) (FIGS. 7(b) and 7(c)). Results of a detachment assay indicated that the TW/GSNsiRNA cells did not differ in strength of cell-substratum adhesion from the TW/siMock cells (FIG. 7(d)). Meanwhile, results of a wound-healing assay indicated that a cell movement of the TW/GSNsiRNA cells were reduced compared to that of the TW/siMock cells, and extremely lowered accompanied by suppressed expression of gelsolin so as to be similar to a cell migration of parent TYK cells (FIG. 7(e)).

Further, in order to determine how expressions of actinin/cofilin are correlated to that of gelsolin, expression levels of gelsolin protein in TW/ACTN-CFL cells and TW/Mock cells were determined. As a result, constitutive expressions of α-actinin 1 and cofilin suppressed the expression of gelsolin (FIG. 6(f)). Conversely, an suppressed expression of gelsolin caused an increase in the expressions of α-actinin 1 and cofilin (FIG. 7(f)).

In summary, a constitutive expression of the WT1 17AA(−)/KTS(−) isoform performs a down-regulation of both expressions of α-actinin 1 and cofilin, and a up-regulation of an expression of gelsoline. Moreover, α-actinin 1/cofilin expression and gelsolin expression are mutually regulated in the downstream signaling of the WT1 17AA(−)/KTS(−) isoform. That is to say, functions of the WT1 17AA(−)/KTS(−) isoform (e.g., induction of a morphological change in cell, weakening of cell-substratum adhesion, enhancement of cell migration) are wholly or partly performed via the regulations of α-actinin 1/cofilin and gelsolin.

Based on the results above, it was found out that the WT1 17AA(−)/KTS(−) isoform fulfill an oncogene-like function in a cell forming a solid tumor.

Example 6

Figure 9:
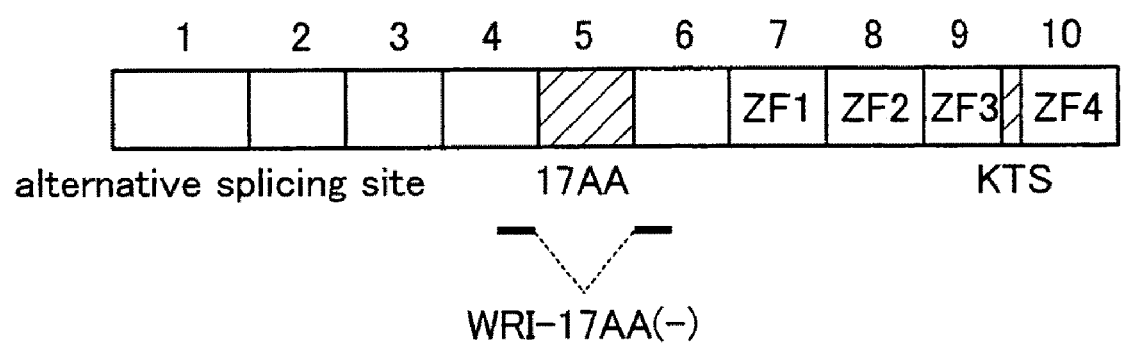
FIG. 9 is a schematic view showing a target site of a siRNA vector for specifically suppressing an expression of WT1 17AA(−) isoform.

Induction of Apoptosis in Solid Tumor by Suppressing Expression of WT1 17AA(−)/KTS(−) Isoform Constructed was a siRNA vector that specifically suppresses expression of WT1 17AA(−) isoform. Concretely, as shown in FIG. 9, the siRNA was constructed to target a sequence 5'-AGCCACCTTAAAGGGCCACAGCA-CAGGGTA-3' (SEQ ID NO: 26) in the WT1 17AA(−) isoform so that a region formed by splicing a 17AA region out becomes a target sequence. Synthesized were such oligo-DNA that restriction sites are added to both ends of a oligonucleotide (SEQ ID NO: 27) composed of a sense strand (5'-agccaccuuaaagggccgcgguauagggua (SEQ ID NO:29; a sequence in which a sense strand of the target sequence is mutated at an underlined part)—cttcctgtca (SEQ ID NO:31; a loop sequence of human pre-miR-23)—uacccugugcugugg cccuuuaagguggcu (SEQ ID NO:30; an antisense strand of the target sequence)), and oligo-DNA which is complementary to the oligo-DNA above (Japan Bio Service). After an annealing, these oligo-DNA were inserted to a downstream site of a tRNAval promoter in piGENEtRNA Pur Vector (Clonetech), thereby obtaining a WRI-17AA(−) siRNA vector which transcribes dsRNA including the loop sequence.

WT1-expressing cell lines (fibrosarcoma cells HT-1080, stomach cancer cells AZ-521, and glioma cells A172) and a WT1-nonexpressing cell line (lung cancer cells PC-14) were incubated at the presence of 5% $CO_2$ at 37° C. in a DMEM medium including 10% FBS.

A WT1-siRNA expression vector or a Mock vector (2 µg) was transduced, by a lipofection method using FuGENE6 (Roche), into the cells (with an amount of $2 \times 10^5$ cells) that were plated in a 6-well plate and then incubated for one day. The cells were treated with trypsin three days after the transduction. The number of the cells was counted, and then the cells were subjected to a flow cytometric analysis.

After being washed with PBS, cells with an amount of $1.0 \times 10^5$ were stained by reacting with Annexin V-FITC and PI at a room temperature for 15 minutes with the use of MEBCYTO Apoptosis kit (Medical and Biological Laboratories CO., Ltd, Nagoya, Japan). The cells were analyzed by using FACScan flowcytometer (Becton Dickinson, San Jose, Calif.). An Annexin V-FITC positive/PI negative cell was regarded as an apoptotic cell.

Figure 10:
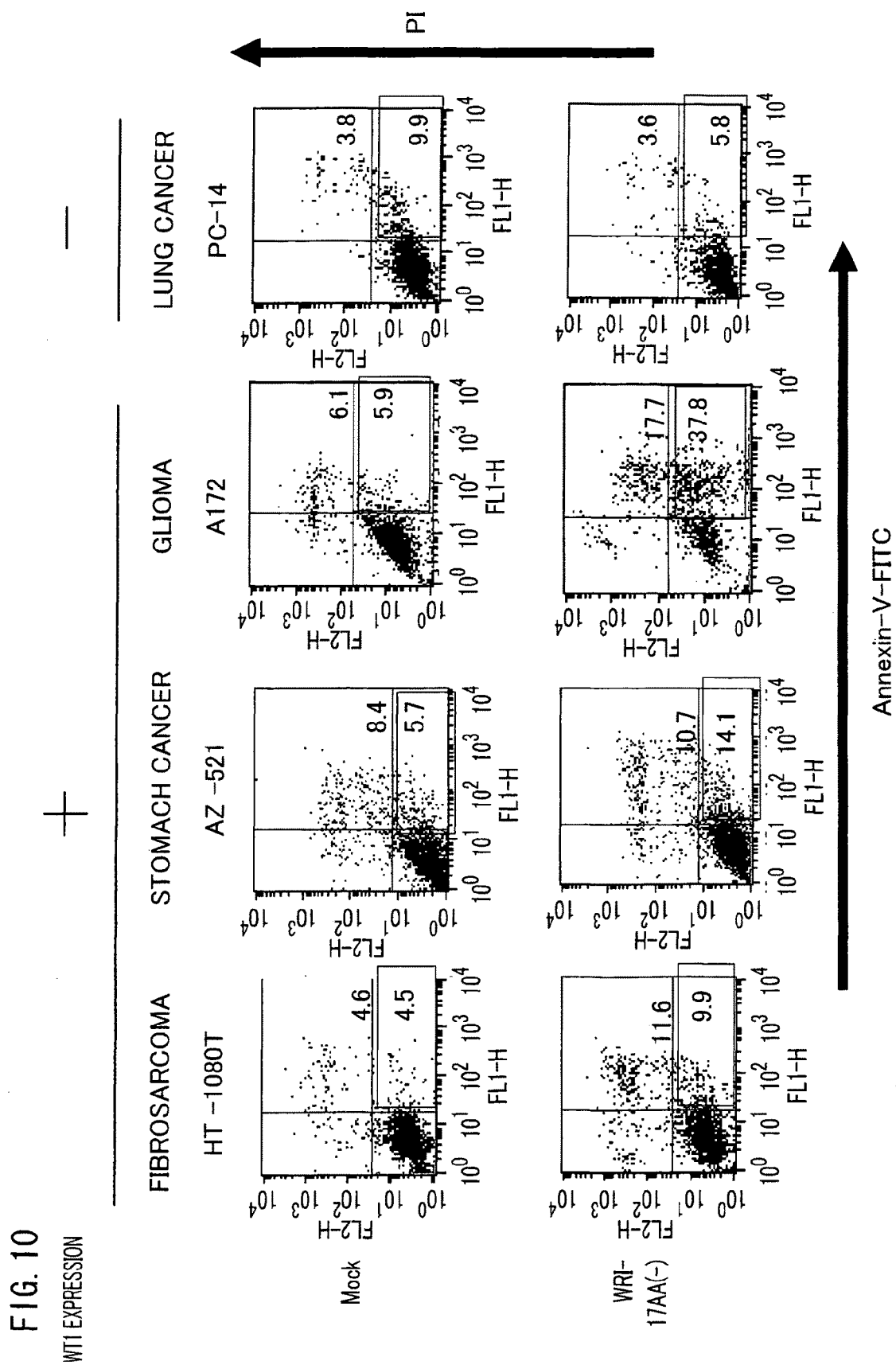
FIG. 10 is a view showing the presence or absence of apoptosis induction caused by transducing a WT1 17AA(−) isoform-specific siRNA vector into WT1-expressing cells or WT1-nonexpressing cells.

In the WT1-expressing cells (HT-1080 cell, AZ-521 cell, and A172 cell), apoptosis was induced due to the transduction of a WT1 17AA(−) isoform-specific vector WRI-17AA(−). On the other hand, apoptosis was not induced in the WT1-nonexpressing cell line PC-14 although the WRI-17AA(−) was transduced (FIG. 10).

Example 7

Figure 11:
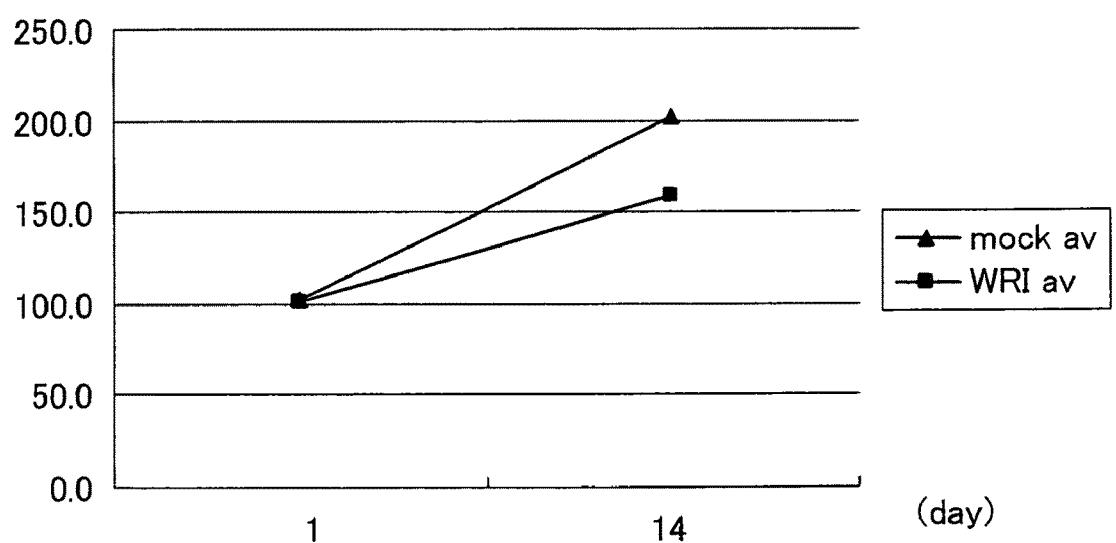
FIG. 11 is a view showing suppression of a tumor formation in a mouse transplanted subcutaneously with a human tumor cell caused by suppressing an expression of WT1 17AA(−) isoform.

Suppression of Solid Tumor Formation In Vivo by Suppressing Expression of WT1 17AA(−) Isoform FIG. 11 shows sizes of tumors, formed by injected HT-1080 cells, in two out of a group of mice administered with WT1-shRNA (WRI) targeting at WT1 17AA(−) isoform and in two out of a group of mice administered with a control shRNA vector (mock). As shown in FIG. 11, a tumor growth was suppressed in vivo by suppressing an expression of the WT1 17AA(−) isoform. Note that averages of the sizes in each group were shown in FIG. 11.

As described above, by applying siRNA that specifically suppresses an expression of WT1 17AA(−) isoform to a solid tumor cell in which WT1 17AA(−)/KTS(−) isoform fulfills an oncogene-like function, a cell death that occurs specifically in the tumor cell can be induced. That is, an anticancer function can be attained.

By using the present invention, it is possible to induce apoptosis specifically in a cell forming a solid tumor. Therefore, it is possible to treat the solid tumor.

Specific embodiments or examples implemented in BEST MODE FOR CARRYING OUT THE INVENTION and EXAMPLE only show technical features of the present invention and are not intended to limit the scope of the invention. Variations can be effected within the spirit of the present invention and the scope of the following claims.

INDUSTRIAL APPLICABILITY

Since a WT1 gene is highly expressed specifically in a cancer cell, a cell death induced by suppressing an expression of WT1 17AA(−) isoform is caused specifically in the cancer call, but not in a normal cell. Therefore, the present invention is highly useful in fields of medicine and pharmacy as a fundamental technology for developing a molecular-targeted therapy specific to the cancer cell.

The invention claimed is:

1. An isolated polynucleotide of 15 to 49 bases in length comprising at least 15 contiguous bases in the nucleotide sequence of SEQ ID NO:26 that include the nucleotide sequence of SEQ ID NO:27.

2. A polynucleotide consisting of the nucleotide sequence of SEQ ID NO:26.

3. A medical composition for treating a solid tumor, the composition comprising any one of:
   (a) a double-stranded RNA consisting of 15 to 49 base pairs,
   (b) a DNA encoding the double-stranded RNA, or
   (c) a vector comprising the DNA;
   wherein the double-stranded RNA can specifically inhibit expression of WT1 17AA(−) isoform without inhibiting expression of WT1 17AA(+) isoform, and wherein the double-stranded RNA comprises:
      (i) a first RNA comprising bases that are the complement of at least 15 contiguous bases in the nucleotide sequence of SEQ ID NO:26 that include the nucleotide sequence of SEQ ID NO:27 and
      (ii) a second RNA complementary to the first RNA.

4. The medical composition according to claim 3, wherein DNA encoding the second RNA hybridizes under a stringent condition with a polynucleotide having at least 15 contiguous bases in the nucleotide sequence of SEQ ID NO:26 and including the nucleotide sequence of SEQ ID NO:27.

5. The medical composition according to claim 3, wherein the second RNA includes at least 15 contiguous bases in the nucleotide sequence of SEQ ID NO:29.

6. The medical composition according to claim 3, wherein the first RNA includes at least 15 contiguous bases in the nucleotide sequence of SEQ ID NO:30.

7. The medical composition according to claim 3, wherein the DNA encoding the double-stranded RNA includes the nucleotide sequence of SEQ ID NO:27.

8. The medical composition according to claim 3, wherein the double-stranded RNA comprises the nucleotide sequence of SEQ ID NO:29 hybridized to the nucleotide sequence of SEQ ID NO:30.

9. A medical kit for treating a solid tumor, the kit comprising any one of:
   (a) a double-stranded RNA consisting of 15 to 49 base pairs,
   (b) a DNA encoding the double-stranded RNA, or
   (c) a vector comprising the DNA;
   wherein the double-stranded RNA can specifically inhibit expression of WT1 17AA(−) isoform without inhibiting expression of WT1 17AA(+) isoform, and wherein the double-stranded RNA comprises:
      (i) a first RNA comprising bases that are the complement of at least 15 contiguous bases in the nucleotide sequence of SEQ ID NO:26 that include the nucleotide sequence of SEQ ID NO:27 and
      (ii) a second RNA complementary to the first RNA.

10. A method for treating a solid tumor, the method comprising:
   administering a double-stranded RNA to a cell forming the solid tumor; wherein the double-stranded RNA can specifically inhibit expression of WT1 17AA(−) isoform without inhibiting expression of WT1 17AA(+) isoform, and wherein the double-stranded RNA is composed of (i) a first RNA of 15 to 49 bases in length comprising a nucleotide sequence that is the complement of at least 15 contiguous bases in the nucleotide sequence of SEQ ID NO:26 that include the nucleotide sequence of SEQ ID NO:27 and (ii) a second RNA complementary to the first RNA.

11. The method according to claim 10, wherein the administering is carried out by transducing the target cell with a vector comprising a polynucleotide encoding the first RNA and the second RNA.

12. The method according to claim 10, wherein the double-stranded RNA is 15 to 30 base pairs in length.

13. The method according to claim 11, wherein the double-stranded RNA is 15 to 30 base pairs in length.

14. The polynucleotide according to claim 1, wherein the polynucleotide is 15 to 30 bases in length.

15. The medical composition according to claim 3, wherein the double-stranded RNA is 15 to 30 base pairs in length.

16. The medical kit according to claim 9, wherein the double-stranded RNA is 15 to 30 base pairs in length.

17. A double-stranded RNA of 15 to 49 base pairs in length, the double-stranded RNA comprising bases that are the complement of at least 15 contiguous bases in the nucleotide sequence of SEQ ID NO:26 that include the nucleotide sequence of SEQ ID NO:27, wherein the double-stranded RNA can specifically inhibit expression of WT1 17AA(−) isoform without inhibiting expression of WT1 17AA(+) isoform.

18. A method for treating a solid tumor, the method comprising administering the double-stranded RNA according to claim 17 to a cell forming the solid tumor.

* * * * *

SEQUENCE LISTING

```
<160> NUMBER OF SEQ ID NOS: 39

<210> SEQ ID NO 1
<211> LENGTH: 21
<212> TYPE: DNA
<213> ORGANISM: Artificial Sequence
<220> FEATURE:
<223> OTHER INFORMATION: Artificially Synthesized DNA Sequence

<400> SEQUENCE: 1
ctttccagcc atatcgccaa c                                            21

<210> SEQ ID NO 2
<211> LENGTH: 19
<212> TYPE: DNA
<213> ORGANISM: Artificial Sequence
<220> FEATURE:
<223> OTHER INFORMATION: Artificially Synthesized DNA Sequence

<400> SEQUENCE: 2
ttctctgcct cgctggctc                                               19

<210> SEQ ID NO 3
<211> LENGTH: 18
<212> TYPE: DNA
<213> ORGANISM: Artificial Sequence
<220> FEATURE:
```

<223> OTHER INFORMATION: Artificially Synthesized DNA Sequence

<400> SEQUENCE: 3
ggccagaaat gttcggtg                                                    18

<210> SEQ ID NO 4
<211> LENGTH: 18
<212> TYPE: DNA
<213> ORGANISM: Artificial Sequence
<220> FEATURE:
<223> OTHER INFORMATION: Artificially Synthesized DNA Sequence

<400> SEQUENCE: 4
acgggaggga tatgggta                                                    18

<210> SEQ ID NO 5
<211> LENGTH: 22
<212> TYPE: DNA
<213> ORGANISM: Artificial Sequence
<220> FEATURE:
<223> OTHER INFORMATION: Artificially Synthesized DNA Sequence

<400> SEQUENCE: 5
gactcacctg ggtactggta tg                                               22

<210> SEQ ID NO 6
<211> LENGTH: 22
<212> TYPE: DNA
<213> ORGANISM: Artificial Sequence
<220> FEATURE:
<223> OTHER INFORMATION: Artificially Synthesized DNA Sequence

<400> SEQUENCE: 6
atcgctcttc acctgttgat ag                                               22

<210> SEQ ID NO 7
<211> LENGTH: 19
<212> TYPE: DNA
<213> ORGANISM: Artificial Sequence
<220> FEATURE:
<223> OTHER INFORMATION: Artificially Synthesized DNA Sequence

<400> SEQUENCE: 7
cagtcgccaa aggagtctg                                                   19

<210> SEQ ID NO 8
<211> LENGTH: 21
<212> TYPE: DNA
<213> ORGANISM: Artificial Sequence
<220> FEATURE:
<223> OTHER INFORMATION: Artificially Synthesized DNA Sequence

<400> SEQUENCE: 8
gtagtccttg cgacagtagg c                                                21

<210> SEQ ID NO 9
<211> LENGTH: 18
<212> TYPE: DNA
<213> ORGANISM: Artificial Sequence
<220> FEATURE:
<223> OTHER INFORMATION: Artificially Synthesized DNA Sequence

<400> SEQUENCE: 9
ggagccgaag aaatcgtg                                                    18

<210> SEQ ID NO 10

```
<211> LENGTH: 19
<212> TYPE: DNA
<213> ORGANISM: Artificial Sequence
<220> FEATURE:
<223> OTHER INFORMATION: Artificially Synthesized DNA Sequence

<400> SEQUENCE: 10
ctgctcgttc tcctggttg                                                  19

<210> SEQ ID NO 11
<211> LENGTH: 18
<212> TYPE: DNA
<213> ORGANISM: Artificial Sequence
<220> FEATURE:
<223> OTHER INFORMATION: Artificially Synthesized DNA Sequence

<400> SEQUENCE: 11
ggaaagtcag caagcagg                                                   18

<210> SEQ ID NO 12
<211> LENGTH: 18
<212> TYPE: DNA
<213> ORGANISM: Artificial Sequence
<220> FEATURE:
<223> OTHER INFORMATION: Artificially Synthesized DNA Sequence

<400> SEQUENCE: 12
tgtgcggaaa ggagaagc                                                   18

<210> SEQ ID NO 13
<211> LENGTH: 22
<212> TYPE: DNA
<213> ORGANISM: Artificial Sequence
<220> FEATURE:
<223> OTHER INFORMATION: Artificially Synthesized DNA Sequence

<400> SEQUENCE: 13
tggctacctg gaactgctgg ac                                              22

<210> SEQ ID NO 14
<211> LENGTH: 23
<212> TYPE: DNA
<213> ORGANISM: Artificial Sequence
<220> FEATURE:
<223> OTHER INFORMATION: Artificially Synthesized DNA Sequence

<400> SEQUENCE: 14
tccagctctc gttccttccg aag                                             23

<210> SEQ ID NO 15
<211> LENGTH: 23
<212> TYPE: DNA
<213> ORGANISM: Artificial Sequence
<220> FEATURE:
<223> OTHER INFORMATION: Artificially Synthesized DNA Sequence

<400> SEQUENCE: 15
agtcttcaac gccagaggag gtg                                             23

<210> SEQ ID NO 16
<211> LENGTH: 22
<212> TYPE: DNA
<213> ORGANISM: Artificial Sequence
<220> FEATURE:
<223> OTHER INFORMATION: Artificially Synthesized DNA Sequence

<400> SEQUENCE: 16
```

```
gtgcagcggt ccttgacctc ct                                              22
```

<210> SEQ ID NO 17
<211> LENGTH: 22
<212> TYPE: DNA
<213> ORGANISM: Artificial Sequence
<220> FEATURE:
<223> OTHER INFORMATION: Artificially Synthesized DNA Sequence

<400> SEQUENCE: 17

```
aggagttgat gctgcggctg ca                                              22
```

<210> SEQ ID NO 18
<211> LENGTH: 22
<212> TYPE: DNA
<213> ORGANISM: Artificial Sequence
<220> FEATURE:
<223> OTHER INFORMATION: Artificially Synthesized DNA Sequence

<400> SEQUENCE: 18

```
gtggatgatg tcattgtggg tc                                              22
```

<210> SEQ ID NO 19
<211> LENGTH: 23
<212> TYPE: DNA
<213> ORGANISM: Artificial Sequence
<220> FEATURE:
<223> OTHER INFORMATION: Artificially Synthesized DNA Sequence

<400> SEQUENCE: 19

```
accaccagtc attcctccaa cag                                             23
```

<210> SEQ ID NO 20
<211> LENGTH: 23
<212> TYPE: DNA
<213> ORGANISM: Artificial Sequence
<220> FEATURE:
<223> OTHER INFORMATION: Artificially Synthesized DNA Sequence

<400> SEQUENCE: 20

```
ggcaaggtgg gatgcattcc atc                                             23
```

<210> SEQ ID NO 21
<211> LENGTH: 22
<212> TYPE: DNA
<213> ORGANISM: Artificial Sequence
<220> FEATURE:
<223> OTHER INFORMATION: Artificially Synthesized DNA Sequence

<400> SEQUENCE: 21

```
tggtgccttc aagaccttca cc                                              22
```

<210> SEQ ID NO 22
<211> LENGTH: 24
<212> TYPE: DNA
<213> ORGANISM: Artificial Sequence
<220> FEATURE:
<223> OTHER INFORMATION: Artificially Synthesized DNA Sequence

<400> SEQUENCE: 22

```
gtcacctgag agggttgagt aaac                                            24
```

<210> SEQ ID NO 23
<211> LENGTH: 20
<212> TYPE: DNA
<213> ORGANISM: Artificial Sequence
<220> FEATURE:

<223> OTHER INFORMATION: Artificially Synthesized DNA Sequence

<400> SEQUENCE: 23
gccaaaaggg tcatcatctc                                          20

<210> SEQ ID NO 24
<211> LENGTH: 21
<212> TYPE: DNA
<213> ORGANISM: Artificial Sequence
<220> FEATURE:
<223> OTHER INFORMATION: Artificially Synthesized DNA Sequence

<400> SEQUENCE: 24
gtagaggcag ggatgatgtt c                                        21

<210> SEQ ID NO 25
<211> LENGTH: 29
<212> TYPE: RNA
<213> ORGANISM: Artificial Sequence
<220> FEATURE:
<223> OTHER INFORMATION: Artificially Synthesized RNA Sequence

<400> SEQUENCE: 25
uccaggauga agcagucgcc auuguugaa                                29

<210> SEQ ID NO 26
<211> LENGTH: 30
<212> TYPE: DNA
<213> ORGANISM: Artificial Sequence
<220> FEATURE:
<223> OTHER INFORMATION: Artificially Synthesized DNA Sequence

<400> SEQUENCE: 26
agccacctta aagggccaca gcacagggta                               30

<210> SEQ ID NO 27
<211> LENGTH: 10
<212> TYPE: DNA
<213> ORGANISM: Artificial Sequence
<220> FEATURE:
<223> OTHER INFORMATION: Artificially Synthesized DNA Sequence

<400> SEQUENCE: 27
aagggccaca                                                     10

<210> SEQ ID NO 28
<211> LENGTH: 70
<212> TYPE: DNA
<213> ORGANISM: Artificial Sequence
<220> FEATURE:
<223> OTHER INFORMATION: Artificially Synthesized DNA and RNA Sequence

<400> SEQUENCE: 28
agccaccuua aagggccgcg guauagggua cttcctgtca uacccugugc uguggcccuu    60 uaaggugggcu                                                        70

<210> SEQ ID NO 29
<211> LENGTH: 30
<212> TYPE: RNA
<213> ORGANISM: Artificial Sequence
<220> FEATURE:
<223> OTHER INFORMATION: Artificially Synthesized RNA Sequence

<400> SEQUENCE: 29
agccaccuua aagggccgcg guauagggua                               30

<210> SEQ ID NO 30
<211> LENGTH: 30
<212> TYPE: RNA
<213> ORGANISM: Artificial Sequence
<220> FEATURE:
<223> OTHER INFORMATION: Artificially Synthesized RNA Sequence

<400> SEQUENCE: 30
uacccugugc uguggcccuu uaagguggcu                                       30

<210> SEQ ID NO 31
<211> LENGTH: 10
<212> TYPE: DNA
<213> ORGANISM: Artificial Sequence
<220> FEATURE:
<223> OTHER INFORMATION: Artificially Synthesized DNA Sequence

<400> SEQUENCE: 31
cttcctgtca                                                             10

<210> SEQ ID NO 32
<211> LENGTH: 3029
<212> TYPE: DNA
<213> ORGANISM: Homo sapiens

<400> SEQUENCE: 32
ccaggcagct ggggtaagga gttcaaggca gcgcccacac ccgggggctc tccgcaaccc       60
gaccgcctgt ccgctccccc acttcccgcc ctccctccca cctactcatt cacccaccca      120
cccacccaga gccgggacgg cagcccaggc gcccgggccc cgccgtctcc tcgccgcgat      180
cctggacttc ctcttgctgc aggacccggc ttccacgtgt gtcccggagc cggcgtctca      240
gcacacgctc cgctccgggc ctgggtgcct acagcagcca gagcagcagg gagtccggga      300
cccgggcggc atctgggcca agttaggcgc gccgaggcc agcgctgaac gtctccaggg       360
ccggaggagc cgcggggcgt ccgggtctga gccgcagcaa atgggctccg acgtgcggga      420
cctgaacgcg ctgctgcccg ccgtcccctc cctgggtggc ggcggcggct gtgccctgcc      480
tgtgagcggc gcggcgcagt gggcgccggt gctggacttt gcgcccccgg gcgcttcggc      540
ttacgggtcg ttgggcggcc ccgcgccgcc accggctccg ccgccacccc gccgccgcc       600 gcctcactcc ttcatcaaac aggagccgag ctggggcggc gcggagccgc acgaggagca      660
gtgcctgagc gccttcactg tccactttc cggccagttc actggcacag ccggagcctg      720
tcgctacggg cccttcggtc ctcctccgcc cagccaggcg tcatccggcc aggccaggat      780
gtttcctaac gcgccctacc tgcccagctg cctcgagagc cagcccgcta ttcgcaatca      840
gggttacagc acgtcacct tcgacgggac gcccagctac ggtcacacgc ctcgcaccg      900 tgcggcgcag ttccccaacc actcattcaa gcatgaggat cccatgggcc agcagggctc      960
gctgggtgag cagcagtact cggtgccgcc ccggtctat ggctgccaca ccccaccga      1020 cagctgcacc ggcagccagg ctttgctgct gaggacgccc tacagcagtg acaatttata     1080
ccaaatgaca tccagcttg aatgcatgac ctggaatcag atgaacttag gagccacctt     1140
aaagggagtt gctgctggga gctccagctc agtgaaatgg acagaagggc agagcaacca     1200
cagcacaggg tacgagagcg ataaccacac aacgcccatc ctctgcggag cccaatacag     1260
aatacacacg cacggtgtct tcagaggcat tcaggatgtg cgacgtgtgc ctggagtagc     1320
cccgactctt gtacggtcgg catctgagac cagtgagaaa cgccccttca tgtgtgctta     1380
cccaggctgc aataagagat attttaagct gtcccactta cagatgcaca gcaggaagca     1440

-continued

```
cactggtgag aaaccatacc agtgtgactt caaggactgt gaacgaaggt tttctcgttc    1500
agaccagctc aaaagacacc aaaggagaca tacaggtgtg aaaccattcc agtgtaaaac    1560
ttgtcagcga aagttctccc ggtccgacca cctgaagacc cacaccagga ctcatacagg    1620
taaaacaagt gaaaagccct tcagctgtcg gtggccaagt tgtcagaaaa agtttgcccg    1680
gtcagatgaa ttagtccgcc atcacaacat gcatcagaga acatgaccca aactccagct    1740
ggcgctttga ggggtctccc tcggggaccg ttcagtgtcc caggcagcac agtgtgtgaa    1800
ctgctttcaa gtctgactct ccactcctcc tcactaaaaa ggaaacttca gttgatcttc    1860
ttcatccaac ttccaagaca agataccggt gcttctggaa actaccaggt gtgcctggaa    1920
gagttggtct ctgccctgcc tacttttagt tgactcacag gccctggaga agcagctaac    1980
aatgtctggt tagttaaaag cccattgcca tttggtgtgg attttctact gtaagaagag    2040
ccatagctga tcatgtcccc ctgacccttc ccttcttttt ttatgctcgt tttcgctggg    2100
gatggaatta ttgtaccatt ttctatcatg gaatatttat aggccagggc atgtgtatgt    2160
gtctgctaat gtaaactttg tcatggtttc catttactaa cagcaacagc aagaaataaa    2220
tcagagagca aggcatcggg ggtgaatctt gtctaacatt cccgaggtca gccaggctgc    2280
taacctggaa agcaggatgt agttctgcca ggcaactttt aaagctcatg catttcaagc    2340
agctgaagaa aaaatcagaa ctaaccagta cctctgtata gaaatctaaa agaattttac    2400
cattcagtta attcaatgtg aacactggca cactgctctt aagaaactat gaagatctga    2460
gatttttttg tgtatgtttt tgactctttt gagtggtaat catatgtgtc tttatagatg    2520 tacataccte cttgcacaaa tggaggggaa ttcattttca tcactgggag tgtccttagt    2580
gtataaaaac catgctggta tatggcttca agttgtaaaa atgaaagtga ctttaaaaga    2640
aaatagggga tggtccagga tctccactga taagactgtt tttaagtaac ttaaggacct    2700
ttgggtctac aagtatatgt gaaaaaaatg agacttactg ggtgaggaaa tccattgttt    2760
aaagatggtc gtgtgtgtgt gtgtgtgtgt gtgtgtgtgt gtgttgtgtt gtgttttgtt    2820
ttttaaggga gggaatttat tatttaccgt tgcttgaaat tactgtgtaa atatatgtct    2880
gataatgatt tgctctttga caactaaaat taggactgta taagtactag atgcatcact    2940
gggtgttgat cttacaagat attgatgata acacttaaaa ttgtaacctg catttttcac    3000
tttgctctca attaaagtct attcaaaag                                      3029
```

<210> SEQ ID NO 33
<211> LENGTH: 449
<212> TYPE: PRT
<213> ORGANISM: Homo sapiens

<400> SEQUENCE: 33

```
Met Gly Ser Asp Val Arg Asp Leu Asn Ala Leu Leu Pro Ala Val Pro
  1               5                  10                  15

Ser Leu Gly Gly Gly Gly Gly Cys Ala Leu Pro Val Ser Gly Ala Ala
             20                  25                  30

Gln Trp Ala Pro Val Leu Asp Phe Ala Pro Pro Gly Ala Ser Ala Tyr
         35                  40                  45

Gly Ser Leu Gly Gly Pro Ala Pro Pro Pro Ala Pro Pro Pro Pro Pro
     50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95
```

```
Ser Gly Gln Phe Thr Gly Thr Ala Gly Ala Cys Arg Tyr Gly Pro Phe
            100                 105                 110
Gly Pro Pro Pro Ser Gln Ala Ser Ser Gly Gln Ala Arg Met Phe
        115                 120                 125
Pro Asn Ala Pro Tyr Leu Pro Ser Cys Leu Glu Ser Gln Pro Ala Ile
130                 135                 140
Arg Asn Gln Gly Tyr Ser Thr Val Thr Phe Asp Gly Thr Pro Ser Tyr
145                 150                 155                 160
Gly His Thr Pro Ser His His Ala Ala Gln Phe Pro Asn His Ser Phe
                165                 170                 175
Lys His Glu Asp Pro Met Gly Gln Gly Ser Leu Gly Glu Gln Gln
            180                 185                 190
Tyr Ser Val Pro Pro Val Tyr Gly Cys His Thr Pro Thr Asp Ser
            195                 200                 205
Cys Thr Gly Ser Gln Ala Leu Leu Leu Arg Thr Pro Tyr Ser Ser Asp
210                 215                 220
Asn Leu Tyr Gln Met Thr Ser Gln Leu Glu Cys Met Thr Trp Asn Gln
225                 230                 235                 240
Met Asn Leu Gly Ala Thr Leu Lys Gly Val Ala Ala Gly Ser Ser Ser
                245                 250                 255
Ser Val Lys Trp Thr Glu Gly Gln Ser Asn His Ser Thr Gly Tyr Glu
            260                 265                 270
Ser Asp Asn His Thr Thr Pro Ile Leu Cys Gly Ala Gln Tyr Arg Ile
            275                 280                 285
His Thr His Gly Val Phe Arg Gly Ile Gln Asp Val Arg Arg Val Pro
            290                 295                 300
Gly Val Ala Pro Thr Leu Val Arg Ser Ala Ser Glu Thr Ser Glu Lys
305                 310                 315                 320
Arg Pro Phe Met Cys Ala Tyr Pro Gly Cys Asn Lys Arg Tyr Phe Lys
                325                 330                 335
Leu Ser His Leu Gln Met His Ser Arg Lys His Thr Gly Glu Lys Pro
            340                 345                 350
Tyr Gln Cys Asp Phe Lys Asp Cys Glu Arg Arg Phe Ser Arg Ser Asp
            355                 360                 365
Gln Leu Lys Arg His Gln Arg Arg His Thr Gly Val Lys Pro Phe Gln
    370                 375                 380
Cys Lys Thr Cys Gln Arg Lys Phe Ser Arg Ser Asp His Leu Lys Thr
385                 390                 395                 400
His Thr Arg Thr His Thr Gly Lys Thr Ser Glu Lys Pro Phe Ser Cys
                405                 410                 415
Arg Trp Pro Ser Cys Gln Lys Lys Phe Ala Arg Ser Asp Glu Leu Val
            420                 425                 430
Arg His His Asn Met His Gln Arg Asn Met Thr Lys Leu Gln Leu Ala
    435                 440                 445
Leu

<210> SEQ ID NO 34
<211> LENGTH: 3020
<212> TYPE: DNA
<213> ORGANISM: Homo sapiens

<400> SEQUENCE: 34
ccaggcagct ggggtaagga gttcaaggca gcgcccacac ccggggggctc tccgcaaccc      60
gaccgcctgt ccgctccccc acttcccgcc ctccctccca cctactcatt cacccaccca     120
```

-continued

```
cccacccaga gccgggacgg cagcccaggc gcccgggccc cgccgtctcc tcgccgcgat    180
cctggacttc ctcttgctgc aggacccggc ttccacgtgt gtcccggagc cggcgtctca    240
gcacacgctc cgctccgggc ctgggtgcct acagcagcca gagcagcagg gagtccggga    300
cccggcggga atctgggcca agttaggcgc cgccgaggcc agcgctgaac gtctccaggg    360
ccggaggagc cgcggggcgt ccgggtctga gccgcagcaa atgggctccg acgtgcggga    420
cctgaacgcg ctgctgcccg ccgtcccctc cctgggtggc ggcggcggct gtgccctgcc    480
tgtgagcggc gcggcgcagt gggcgccggt gctggacttt gcgccccggg gcgcttcggc    540
ttacgggtcg ttgggcggcc ccgcgccgcc accggctccg ccgccacccc cgccgccgcc    600
gcctcactcc ttcatcaaac aggagccgag ctggggcggc gcggagccgc acgaggagca    660
gtgcctgagc gccttcactg tccactttc cggccagttc actggcacag ccggagcctg    720
tcgctacggg cccttcggtc ctcctccgcc cagccaggcg tcatccggcc aggccaggat    780
gtttcctaac gcgccctacc tgcccagctg cctcgagagc cagcccgcta ttcgcaatca    840
gggttacagc acggtcacct tcgacgggac gcccagctac ggtcacacgc cctcgcacca    900
tgcggcgcag ttccccaacc actcattcaa gcatgaggat cccatgggcc agcagggctc    960
gctgggtgag cagcagtact cggtgccgcc cccggtctat ggctgccaca cccccaccga   1020
cagctgcacc ggcagccagg cttttgctgct gaggacgccc tacagcagtg acaatttata   1080
ccaaatgaca tcccagcttg aatgcatgac ctggaatcag atgaacttag gagccacctt   1140
aaagggagtt gctgctggga gctccagctc agtgaaatgg acagaagggc agagcaacca   1200
cagcacaggg tacgagagcg ataaccacac aacgcccatc ctctgcggag cccaatacag   1260
aatacacacg cacggtgtct tcagaggcat tcaggatgtg cgacgtgtgc ctggagtagc   1320
cccgactctt gtacggtcgg catctgagac cagtgagaaa cgcccttca tgtgtgctta   1380 cccaggctgc aataagagat attttaagct gtcccactta cagatgcaca gcaggaagca   1440
cactggtgag aaaccatacc agtgtgactt caaggactgt gaacgaaggt tttctcgttc   1500
agaccagctc aaaagacacc aaaggagaca tacaggtgtg aaaccattcc agtgtaaaac   1560
ttgtcagcga aagttctccc ggtccgacca cctgaagacc cacaccagga ctcatacagg   1620
tgaaaagccc ttcagctgtc ggtggccaag ttgtcagaaa aagtttgccc ggtcagatga   1680
attagtccgc catcacaaca tgcatcagag aaacatgacc aaactccagc tggcgctttg   1740
aggggtctcc ctcggggacc gttcagtgtc ccaggcagca cagtgtgtga actgctttca   1800
agtctgactc tccactcctc ctcactaaaa aggaaacttc agttgatctt cttcatccaa   1860
cttccaagac aagataccgg tgcttctgga aactaccagg tgtgcctgga agagttggtc   1920
tctgccctgc ctactttag ttgactcaca ggccctggag aagcagctaa caatgtctgg   1980
ttagttaaaa gcccattgcc atttggtgtg attttctac tgtaagaaga gccatagctg   2040
atcatgtccc cctgacccctt ccttctttt tttatgctcg ttttcgctgg ggatggaatt   2100
attgtaccat tttctatcat ggaatattta taggccaggg catgtgtatg tgtctgctaa   2160
tgtaaacttt gtcatggttt ccatttacta acagcaacag caagaaataa atcagagagc   2220
aaggcatcgg gggtgaatct tgtctaacat tcccgaggtc agccaggctg ctaacctgga   2280
aagcaggatg tagttctgcc aggcaacttt taaagctcat gcatttcaag cagctgaaga   2340
aaaaatcaga actaaccagt acctctgtat agaaatctaa aagaattta ccattcagtt   2400 aattcaatgt gaacactggc acactgctct taagaaacta tgaagatctg agatttttt   2460 gtgtatgttt ttgactcttt tgagtggtaa tcatatgtgt ctttatagat gtacatacct   2520
```

-continued

```
ccttgcacaa atggagggga attcattttc atcactggga gtgtccttag tgtataaaaa    2580
ccatgctggt atatggcttc aagttgtaaa aatgaaagtg actttaaaag aaaatagggg    2640
atggtccagg atctccactg ataagactgt ttttaagtaa cttaaggacc tttgggtcta    2700
caagtatatg tgaaaaaaat gagacttact gggtgaggaa atccattgtt taaagatggt    2760
cgtgtgtgtg tgtgtgtgtg tgtgtgtgtg tgtgttgtgt tgtgttttgt tttttaaggg    2820
agggaattta ttatttaccg ttgcttgaaa ttactgtgta aatatatgtc tgataatgat    2880
ttgctctttg acaactaaaa ttaggactgt ataagtacta gatgcatcac tgggtgttga    2940
tcttacaaga tattgatgat aacacttaaa attgtaacct gcattttca ctttgctctc     3000 aattaaagtc tattcaaaag                                                 3020
```

<210> SEQ ID NO 35
<211> LENGTH: 446
<212> TYPE: PRT
<213> ORGANISM: Homo sapiens

<400> SEQUENCE: 35

```
Met Gly Ser Asp Val Arg Asp Leu Asn Ala Leu Leu Pro Ala Val
1               5                  10                  15

Ser Leu Gly Gly Gly Gly Cys Ala Leu Pro Val Ser Gly Ala Ala
                20                 25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro
        50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285
```

```
His Thr His Gly Val Phe Arg Gly Ile Gln Asp Val Arg Arg Val Pro
            290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Glu Lys Pro Phe Ser Cys Arg Trp Pro
                405                 410                 415

Ser Cys Gln Lys Lys Phe Ala Arg Ser Asp Glu Leu Val Arg His His
            420                 425                 430

Asn Met His Gln Arg Asn Met Thr Lys Leu Gln Leu Ala Leu
            435                 440                 445

<210> SEQ ID NO 36
<211> LENGTH: 2978
<212> TYPE: DNA
<213> ORGANISM: Homo sapiens

<400> SEQUENCE: 36
ccaggcagct ggggtaagga gttcaaggca gcgcccacac ccgggggctc tccgcaaccc       60
gaccgcctgt ccgctccccc acttcccgcc ctccctccca cctactcatt cacccaccca      120
cccacccaga gccgggacgg cagcccaggc gccgggccc cgccgtctcc tcgccgcgat       180
cctggacttc ctcttgctgc aggacccggc ttccacgtgt gtcccggagc cggcgtctca      240
gcacacgctc cgctccgggc ctgggtgcct acagcagcca gagcagcagg gagtccggga      300
cccgggcggc atctgggcca agttaggcgc cgccgaggcc agcgctgaac gtctccaggg      360
ccggaggagc cgcggggcgt ccgggtctga gccgcagcaa atgggctccg acgtgcggga      420
cctgaacgcg ctgctgcccg ccgtcccctc cctgggtggc ggcggcggct gtgccctgcc      480
tgtgagcggc gcggcgcagt gggcgccggt gctggacttt gcgccccgg gcgcttcggc       540 ttacgggtcg ttgggcggcc ccgcgccgcc accggctccg ccgccacccc cgccgccgcc      600
gcctcactcc ttcatcaaac aggagccgag ctggggcggc gcggagccgc acgaggagca      660
gtgcctgagc gccttcactg tccacttttc cggccagttc actggcacag ccggagcctg      720
tcgctacggg cccttcggtc ctcctccgcc cagccaggcg tcatccggcc aggccaggat      780
gtttcctaac gcgccctacc tgcccagctg cctcgagagc cagcccgcta ttcgcaatca      840
gggttacagc acggtcacct cgacgggac gcccagctac ggtcacacgc cctcgcacca      900
tgcggcgcag ttccccaacc actcattcaa gcatgaggat cccatgggcc agcagggctc      960
gctgggtgag cagcagtact cggtgccgcc ccggtctat ggctgccaca cccccaccga     1020
cagctgcacc ggcagccagg cttttgctgct gaggacgccc tacagcagtg acaatttata      1080
ccaaatgaca tcccagcttg aatgcatgac ctggaatcag atgaacttag gagccacctt     1140
aaagggccac agcacagggt acgagagcga taaccacaca acgccatcc tctgcggagc       1200 ccaatacaga atacacacgc acggtgtctt cagaggcatt caggatgtgc gacgtgtgcc     1260
```

-continued

| | |
|---|---|
| tggagtagcc ccgactcttg tacggtcggc atctgagacc agtgagaaac gcccccttcat | 1320 |
| gtgtgcttac ccaggctgca ataagagata ttttaagctg tcccacttac agatgcacag | 1380 |
| caggaagcac actggtgaga accatacca gtgtgacttc aaggactgtg aacgaaggtt | 1440 |
| ttctcgttca gaccagctca aaagacacca aaggagacat acaggtgtga accattcca | 1500 |
| gtgtaaaact tgtcagcgaa agttctcccg gtccgaccac ctgaagaccc acaccaggac | 1560 |
| tcatacaggt aaaacaagtg aaaagccctt cagctgtcgg tggccaagtt gtcagaaaaa | 1620 |
| gtttgcccgg tcagatgaat tagtccgcca tcacaacatg catcagagaa acatgaccaa | 1680 |
| actccagctg gcgctttgag gggtctccct cggggaccgt tcagtgtccc aggcagcaca | 1740 |
| gtgtgtgaac tgctttcaag tctgactctc cactcctcct cactaaaaag gaaacttcag | 1800 |
| ttgatcttct tcatccaact tccaagacaa gataccggtg cttctggaaa ctaccaggtg | 1860 |
| tgcctggaag agttggtctc tgccctgcct acttttagtt gactcacagg ccctggagaa | 1920 |
| gcagctaaca atgtctggtt agttaaaagc ccattgccat ttggtgtgga ttttctactg | 1980 |
| taagaagagc catagctgat catgtccccc tgacccttcc cttcttttt tatgctcgtt | 2040 |
| ttcgctgggg atggaattat tgtaccattt tctatcatgg aatatttata ggccagggca | 2100 |
| tgtgtatgtg tctgctaatg taaactttgt catggtttcc atttactaac agcaacagca | 2160 |
| agaaataaat cagagagcaa ggcatcgggg gtgaatcttg tctaacattc ccgaggtcag | 2220 |
| ccaggctgct aacctggaaa gcaggatgta gttctgccag gcaactttta aagctcatgc | 2280 |
| atttcaagca gctgaagaaa aaatcagaac taaccagtac ctctgtatag aaatctaaaa | 2340 |
| gaattttacc attcagttaa ttcaatgtga acactggcac actgctctta agaaactatg | 2400 |
| aagatctgag attttttgt gtatgttttt gactcttttg agtggtaatc atatgtgtct | 2460 |
| ttatagatgt acatacctcc ttgcacaaat ggagggaat tcattttcat cactgggagt | 2520 |
| gtccttagtg tataaaaacc atgctggtat atggcttcaa gttgtaaaaa tgaaagtgac | 2580 |
| tttaaaagaa aataggggat ggtccaggat ctccactgat aagactgttt ttaagtaact | 2640 |
| taaggacctt tgggtctaca agtatatgtg aaaaaaatga gacttactgg gtgaggaaat | 2700 |
| ccattgttta aagatggtcg tgtgtgtgtg tgtgtgtgtg tgtgtgtgtg tgttgtgttg | 2760 |
| tgttttgttt tttaagggag ggaatttatt atttaccgtt gcttgaaatt actgtgtaaa | 2820 |
| tatatgtctg ataatgattt gctctttgac aactaaaatt aggactgtat aagtactaga | 2880 |
| tgcatcactg ggtgttgatc ttacaagata ttgatgataa cacttaaaat tgtaacctgc | 2940 |
| atttttcact ttgctctcaa ttaaagtcta ttcaaaag | 2978 |

<210> SEQ ID NO 37
<211> LENGTH: 432
<212> TYPE: PRT
<213> ORGANISM: Homo sapiens

<400> SEQUENCE: 37

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Gly Ala Ser Ala Tyr
            35                  40                  45

Gly Ser Leu Gly Gly Pro Ala Pro Pro Ala Pro Pro Pro Pro
        50                  55                  60

Pro Pro Pro Pro His Ser Phe Ile Lys Gln Glu Pro Ser Trp Gly Gly
65                  70                  75                  80

```
Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly His Ser Thr Gly Tyr Glu Ser
                245                 250                 255

Asp Asn His Thr Thr Pro Ile Leu Cys Gly Ala Gln Tyr Arg Ile His
            260                 265                 270

Thr His Gly Val Phe Arg Gly Ile Gln Asp Val Arg Arg Val Pro Gly
        275                 280                 285

Val Ala Pro Thr Leu Val Arg Ser Ala Ser Glu Thr Ser Glu Lys Arg
290                 295                 300

Pro Phe Met Cys Ala Tyr Pro Gly Cys Asn Lys Arg Tyr Phe Lys Leu
305                 310                 315                 320

Ser His Leu Gln Met His Ser Arg Lys His Thr Gly Glu Lys Pro Tyr
                325                 330                 335

Gln Cys Asp Phe Lys Asp Cys Glu Arg Arg Phe Ser Arg Ser Asp Gln
            340                 345                 350

Leu Lys Arg His Gln Arg Arg His Thr Gly Val Lys Pro Phe Gln Cys
        355                 360                 365

Lys Thr Cys Gln Arg Lys Phe Ser Arg Ser Asp His Leu Lys Thr His
370                 375                 380

Thr Arg Thr His Thr Gly Lys Thr Ser Glu Lys Pro Phe Ser Cys Arg
385                 390                 395                 400

Trp Pro Ser Cys Gln Lys Lys Phe Ala Arg Ser Asp Glu Leu Val Arg
                405                 410                 415

His His Asn Met His Gln Arg Asn Met Thr Lys Leu Gln Leu Ala Leu
            420                 425                 430
```

<210> SEQ ID NO 38
<211> LENGTH: 2969
<212> TYPE: DNA
<213> ORGANISM: Homo sapiens

<400> SEQUENCE: 38
ccaggcagct ggggtaagga gttcaaggca gcgcccacac ccgggggctc tccgcaaccc    60
gaccgcctgt ccgctccccc acttcccgcc ctccctccca cctactcatt cacccaccca   120
cccacccaga gccgggacgg cagcccaggc gcccgggccc cgccgtctcc tcgccgcgat   180

-continued

| | |
|---|---|
| cctggacttc ctcttgctgc aggacccggc ttccacgtgt gtcccggagc cggcgtctca | 240 |
| gcacacgctc cgctccgggc ctgggtgcct acagcagcca gagcagcagg gagtccggga | 300 |
| cccgggcggc atctgggcca agttaggcgc cgccgaggcc agcgctgaac gtctccaggg | 360 |
| ccggaggagc cgcggggcgt ccgggtctga gccgcagcaa atgggctccg acgtgcggga | 420 |
| cctgaacgcg ctgctgcccg ccgtcccctc cctgggtggc ggcggcggct gtgcctgcc | 480 |
| tgtgagcggc gcggcgcagt gggcgccggt gctggacttt gcgcccccgg gcgcttcggc | 540 |
| ttacgggtcg ttgggcggcc ccgcgccgcc accggctccg ccgccacccc cgccgccgcc | 600 |
| gcctcactcc ttcatcaaac aggagccgag ctggggcggc gcggagccgc acgaggagca | 660 |
| gtgcctgagc gccttcactg tccacttttc cggccagttc actggcacag ccggagcctg | 720 |
| tcgctacggg cccttcggtc ctcctccgcc cagccaggcg tcatccggcc aggccaggat | 780 |
| gtttcctaac gcgccctacc tgcccagctg cctcgagagc cagcccgcta ttcgcaatca | 840 |
| gggttacagc acggtcacct tcgacgggac gcccagctac ggtcacacgc cctcgcacca | 900 |
| tgcggcgcag ttccccaacc actcattcaa gcatgaggat cccatgggcc agcagggctc | 960 |
| gctgggtgag cagcagtact cggtgccgcc cccggtctat ggctgccaca cccccaccga | 1020 |
| cagctgcacc ggcagccagg ctttgctgct gaggacgccc tacagcagtg acaatttata | 1080 |
| ccaaatgaca tcccagcttg aatgcatgac ctggaatcag atgaacttag gagccacctt | 1140 |
| aaagggccac agcacagggt acgagagcga taaccacaca acgcccatcc tctgcggagc | 1200 |
| ccaatacaga atacacacgc acggtgtctt cagaggcatt caggatgtgc gacgtgtgcc | 1260 |
| tggagtagcc ccgactcttg tacggtcggc atctgagacc agtgagaaac gcccttcat | 1320 |
| gtgtgcttac ccaggctgca ataagagata ttttaagctg tcccacttac agatgcacag | 1380 |
| caggaagcac actggtgaga accataccca gtgtgacttc aaggactgtg aacgaaggtt | 1440 |
| ttctcgttca gaccagctca aaagacacca aaggagacat acaggtgtga aaccattcca | 1500 |
| gtgtaaaact tgtcagcgaa agttctcccg gtccgaccac ctgaagaccc acaccaggac | 1560 |
| tcatacaggt gaaaagccct tcagctgtcg gtggccaagt tgtcagaaaa agtttgcccg | 1620 |
| gtcagatgaa ttagtccgcc atcacaacat gcatcagaga aacatgacca aactccagct | 1680 |
| ggcgctttga ggggtctccc tcggggaccg ttcagtgtcc caggcagcac agtgtgtgaa | 1740 |
| ctgcttttcaa gtctgactct ccactcctcc tcactaaaaa ggaaacttca gttgatcttc | 1800 |
| ttcatccaac ttccaagaca agataccggt gcttctggaa actaccaggt gtgcctggaa | 1860 |
| gagttggtct ctgccctgcc tacttttagt tgactcacag gccctggaga agcagctaac | 1920 |
| aatgtctggt tagttaaaag cccattgcca ttttggtgtgg attttctact gtaagaagag | 1980 |
| ccatagctga tcatgtcccc ctgacccttc ccttcttttt ttatgctcgt tttcgctggg | 2040 |
| gatgaaatta ttgtaccatt ttctatcatg gaatatttat aggccagggc atgtgtatgt | 2100 |
| gtctgctaat gtaaactttg tcatggtttc catttactaa cagcaacagc aagaaataaa | 2160 |
| tcagagagca aggcatcggg ggtgaatctt gtctaacatt cccgaggtca gccaggctgc | 2220 |
| taacctggaa agcaggatgt agttctgcca ggcaactttt aaagctcatg catttcaagc | 2280 |
| agctgaagaa aaaatcagaa ctaaccagta cctctgtata gaaatctaaa agattttac | 2340 |
| cattcagtta attcaatgtg aacactgca cactgctctt aagaaactat gaagatctga | 2400 |
| gattttttg tgtatgtttt tgactctttt gagtggtaat catatgtgtc tttatagatg | 2460 |
| tacatacctc cttgcacaaa tggagggggaa ttcattttca tcactgggag tgtccttagt | 2520 |
| gtataaaaac catgctggta tatggcttca agttgtaaaa atgaaagtga ctttaaaaga | 2580 |

```
aaataggtgga tggtccagga tctccactga taagactgtt tttaagtaac ttaaggacct    2640
ttgggtctac aagtatatgt gaaaaaaatg agacttactg ggtgaggaaa tccattgttt    2700
aaagatggtc gtgtgtgtgt gtgtgtgtgt gtgtgtgtgt gtgttgtgtt gtgttttgtt    2760
ttttaaggga gggaatttat tatttaccgt tgcttgaaat tactgtgtaa atatatgtct    2820
gataatgatt tgctctttga caactaaaat taggactgta taagtactag atgcatcact    2880
gggtgttgat cttacaagat attgatgata acacttaaaa ttgtaacctg cattttcac    2940 tttgctctca attaaagtct attcaaaag                                     2969
```

<210> SEQ ID NO 39
<211> LENGTH: 429
<212> TYPE: PRT
<213> ORGANISM: Homo sapiens

<400> SEQUENCE: 39

```
Met Gly Ser Asp Val Arg Asp Leu Asn Ala Leu Leu Pro Ala Val Pro
  1               5                  10                  15

Ser Leu Gly Gly Gly Gly Gly Cys Ala Leu Pro Val Ser Gly Ala Ala
             20                  25                  30

Gln Trp Ala Pro Val Leu Asp Phe Ala Pro Pro Gly Ala Ser Ala Tyr
         35                  40                  45

Gly Ser Leu Gly Gly Pro Ala Pro Pro Pro Ala Pro Pro Pro Pro Pro
     50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly His Ser Thr Gly Tyr Glu Ser
                245                 250                 255

Asp Asn His Thr Thr Pro Ile Leu Cys Gly Ala Gln Tyr Arg Ile His
            260                 265                 270

Thr His Gly Val Phe Arg Gly Ile Gln Asp Val Arg Arg Val Pro Gly
        275                 280                 285

Val Ala Pro Thr Leu Val Arg Ser Ala Ser Glu Thr Ser Glu Lys Arg
    290                 295                 300
```

```
Pro Phe Met Cys Ala Tyr Pro Gly Cys Asn Lys Arg Tyr Phe Lys Leu
305                 310                 315                 320

Ser His Leu Gln Met His Ser Arg Lys His Thr Gly Glu Lys Pro Tyr
                325                 330                 335

Gln Cys Asp Phe Lys Asp Cys Glu Arg Arg Phe Ser Arg Ser Asp Gln
            340                 345                 350

Leu Lys Arg His Gln Arg Arg His Thr Gly Val Lys Pro Phe Gln Cys
        355                 360                 365

Lys Thr Cys Gln Arg Lys Phe Ser Arg Ser Asp His Leu Lys Thr His
        370                 375                 380

Thr Arg Thr His Thr Gly Glu Lys Pro Phe Ser Cys Arg Trp Pro Ser
385                 390                 395                 400

Cys Gln Lys Lys Phe Ala Arg Ser Asp Glu Leu Val Arg His His Asn
            405                 410                 415

Met His Gln Arg Asn Met Thr Lys Leu Gln Leu Ala Leu
            420                 425
```